(12) United States Patent
Chae et al.

(10) Patent No.: US 11,279,726 B2
(45) Date of Patent: Mar. 22, 2022

(54) NORBORNENE-BASED AMPHIPATHIC COMPOUND AND UTILIZATION THEREOF

(71) Applicant: Industry-University Cooperation Foundation Hanyang University Erica Campus, Ansan-si (KR)

(72) Inventors: Pil Seok Chae, Ansan-si (KR); Manabendra Das, Kaiserslautern (DE)

(73) Assignee: Industry-Usiversity Cooperation Foundation Hanyang University Erica Campus, Yeonsu-gu (KR)

( * ) Notice: Subject to any disclaimer, the term of this patent is extended or adjusted under 35 U.S.C. 154(b) by 449 days.

(21) Appl. No.: 16/480,348

(22) PCT Filed: Feb. 10, 2017

(86) PCT No.: PCT/KR2017/001486
§ 371 (c)(1),
(2) Date: Jul. 24, 2019

(87) PCT Pub. No.: WO2018/139698
PCT Pub. Date: Aug. 2, 2018

(65) Prior Publication Data
US 2019/0382434 A1 Dec. 19, 2019

(30) Foreign Application Priority Data
Jan. 24, 2017 (KR) ........................ 10-2017-0011128

(51) Int. Cl.
| C07H 15/203 | (2006.01) |
| G01N 33/68 | (2006.01) |
| C07K 1/113 | (2006.01) |
| C07K 1/14 | (2006.01) |
| C07K 1/30 | (2006.01) |
| C07K 14/705 | (2006.01) |
| C12N 9/12 | (2006.01) |

(52) U.S. Cl.
CPC ............ C07H 15/203 (2013.01); C07K 1/113 (2013.01); C07K 1/14 (2013.01); C07K 1/306 (2013.01); C07K 14/705 (2013.01); C12N 9/1205 (2013.01); G01N 33/68 (2013.01)

(58) Field of Classification Search
None
See application file for complete search history.

(56) References Cited

U.S. PATENT DOCUMENTS

| 2004/0242897 A1 | 12/2004 | Guzaev et al. |
| 2013/0001465 A1 | 1/2013 | Gellman et al. |

FOREIGN PATENT DOCUMENTS

| WO | WO 2018/139698 | 8/2018 |

OTHER PUBLICATIONS

International Search Report and the Written Opinion dated Oct. 24, 2017 From the International Searching Authority Re. Application No. PCT/KR2017/001486 and Its Translation of Search Report Into English. (10 Pages).
Chae et al. "Glucose-Neopentyl Glycol (GNG) Amphiphiles for Membrane Protein Study", ChemComm: Chemical Communications, 49(23): 2287-2289, Mar. 21, 2013.
Chae et al. "Tripod Amphiphiles for Membrane Protein Manipulation", Molecular BioSystems, 6(1): 89-94, Advance Publication Oct. 14, 2009.
Ilker et al. "Modular Norbornene Derivatives for the Preparation of Well-Defined Amphiphilic Polymers: Study of the Lipid Membrane Disruption Activities", Macromolecules, 37(3): 694-700, Published on Web Jan. 16, 2004.
Newstead et al. "Insights Into Outer Membrane Protein Crystallization", Molecular Membrane Biology, 25(8): 631-638, Dec. 2008.
Newstead et al. "Rationalizing Alpha-Helical Membrane Protein Crystallization", Protein Science, 17(3): 466-472, Published Online Jan. 24, 2008.
Privé "Detergents for the Stabilization and Crystallization of Membrane Proteins", Methods, 41(4): 388-397, Apr. 2007.

*Primary Examiner* — Thomas S Heard

(57) ABSTRACT

Provided are a newly developed norbornene-based amphiphilic compound, a method for preparing the same, and a method for extracting, solubilizing, stabilizing, crystallizing or analyzing a membrane protein using the same. In addition, the compound may effectively extract membrane proteins having various structures and characteristics, compared to a conventional compound, from cell membranes, and may be stably stored in an aqueous solution for a long period of time, and therefore may be used in their functional analysis and structural analysis. The structural and functional analyses of membrane proteins are the most noticeable field in biology and chemistry today due to a close relationship to the development of new drugs.

14 Claims, 17 Drawing Sheets a b a b

FIG. 15a
FIG. 15c
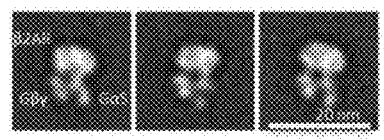
FIG. 15d
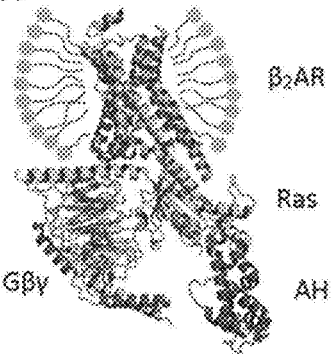
$\beta_2$AR
Ras
G$\beta\gamma$
AH
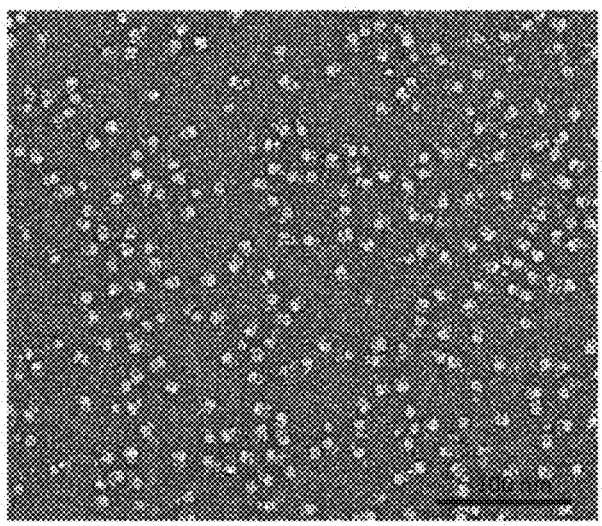
FIG. 15b
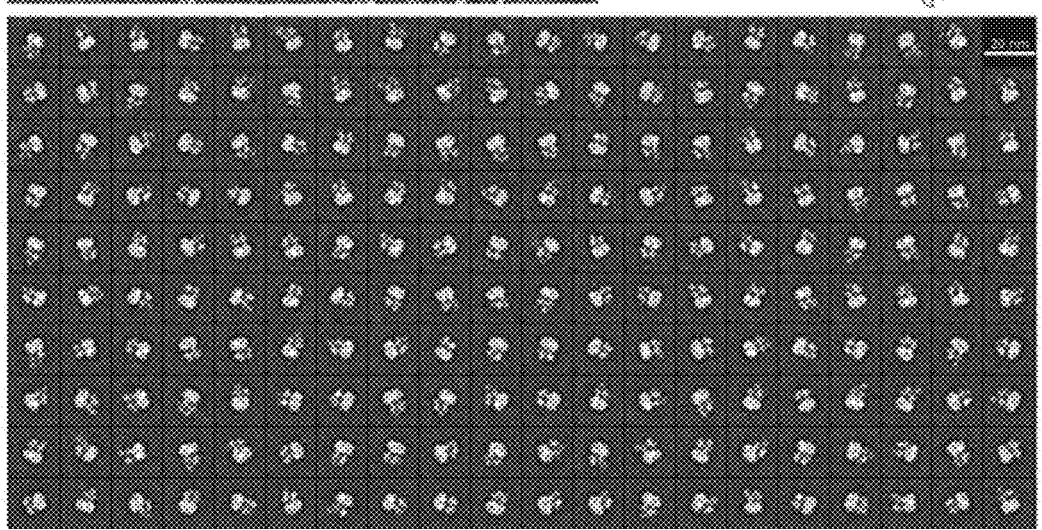

NORBORNENE-BASED AMPHIPATHIC COMPOUND AND UTILIZATION THEREOF

RELATED APPLICATIONS

This application is a National Phase of PCT Patent Application No. PCT/KR2017/001486 having International filing date of Feb. 10, 2017, which claims the benefit of priority of Korean Patent Application No. 10-2017-0011128 filed on Jan. 24, 2017. The contents of the above applications are all incorporated by reference as if fully set forth herein in their entirety.

FIELD AND BACKGROUND OF THE INVENTION

The present invention relates to a newly-developed norbornene-based amphiphilic compound, a method for preparing the same, and a method for extracting, solubilizing, stabilizing, crystallizing or analyzing a membrane protein using the same.

Membrane proteins are essential for biological systems. Because such bio-macromolecules include hydrophilic and hydrophobic domains, an amphiphilic molecule is required for extraction of membrane proteins from a cell membrane and for solubilization and stabilization of the extracted membrane proteins in an aqueous solution.

For structural analysis of membrane proteins, good-quality membrane protein crystals should be obtained, and to this end, structural stability of the membrane proteins in an aqueous solution is required. While there are over a hundred of amphiphilic molecules that have been conventionally used in research of membrane proteins, only five of them have been widely used in research of the structure of membrane proteins. These five amphiphilic molecules include n-octyl-β-D-glucopyranoside (OG), n-nonyl-β-D-glucopyranoside (NG), n-decyl-β-D-maltopyranoside (DM), n-dodecyl-β-D-maltopyranoside (DDM), and lauryldimethylamine-N-oxide (LDAO) (Non-patent literature 1 and Non-patent literature 2). However, since many membrane proteins encapsulated by these molecules tend to be easily denatured and aggregated, thereby rapidly losing their function, there are considerable limitations to research on the function and structure of membrane proteins using such molecules. It is because conventional molecules have a simple chemical structure and thus do not exhibit various characteristics. Therefore, it is necessary to develop a novel amphiphile having novel and excellent characteristics due to a new structure.

Therefore, the inventors developed an amphiphilic compound in which a hydrophobic group and a hydrophilic group are introduced to a core structure of norbornene, confirmed the stability of membrane proteins of the compound, and thus completed the present invention.

(Non-patent literature 1) S. Newstead et al., *Protein Sci.* 17 (2008) 466-472.

(Non-patent literature 2) S. Newstead et al., *Mol. Membr. Biol.* 25 (2008) 631-638.

SUMMARY OF THE INVENTION

An object of the present invention is to provide a compound represented by Formula 1 or Formula 2.

Another object of the present invention is to provide a composition for extracting, solubilizing, stabilizing, crystallizing or analyzing a membrane protein, which includes the above compound.

Still another object of the present invention is to provide a method for preparing the compound.

Yet another object of the present invention is to provide a method for extracting, solubilizing, stabilizing, crystallizing or analyzing a membrane protein using the compound.

An embodiment of the present invention provides a compound represented by Formula 1 or 2 as follows:

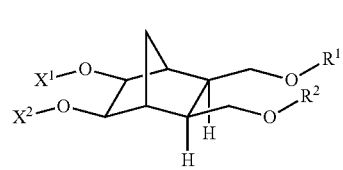

[Formula 1]

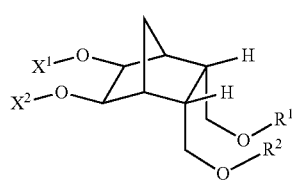

[Formula 2]

In Formula 1 or 2, each of $R^1$ and $R^2$ is independently a substituted or unsubstituted $C_3$ to $C_{30}$ alkyl group, a substituted or unsubstituted $C_3$ to $C_{30}$ cycloalkyl group, or a substituted or unsubstituted $C_3$ to $C_{30}$ aryl group; and $X^1$ and $X^2$ are saccharides.

The compounds of Formulas 1 and 2 of the present invention may be diastereomers for each other, wherein Formula 1 is an exo type, and Formula 2 is an endo type.

The term "saccharide" used herein refers to a carbohydrate compound which is a relatively small molecule with a sweet taste when solubilized in water. The saccharide is classified as a monosaccharide, a disaccharide or a polysaccharide according to the number of molecules constituting sugar.

The saccharide used in the embodiment may be a monosaccharide or disaccharide, and specifically, glucose or maltose, but the present invention is not limited thereto.

The saccharide may act as a hydrophilic group. The compound according to one embodiment of the present invention has a smaller size when forming a complex with a membrane protein by increasing a size of a hydrophilic group and minimizing an increase in length due to connection of two saccharides, which are hydrophilic groups, in parallel. When the size of the complex of the compound and the membrane protein is small, good-quality membrane protein crystals may be obtained (G. G. Prive, *Methods* 2007, 41, 388-397).

In addition, $R^1$ and $R^2$ may act as hydrophobic groups. Two hydrophobic groups are introduced to the compound according to one embodiment of the present invention so as to optimize hydrophile-lipophile balance.

The compound according to one embodiment of the present invention may have a norbornene linker as a core structure. That is, the compound may be an amphiphile having two hydrophilic groups and two hydrophobic groups as a norbornene core structure to have membrane protein stabilization and an excellent performance for crystallization.

Specifically, each of $R^1$ and $R^2$ may be independently a substituted or unsubstituted $C_3$ to $C_{30}$ alkyl group; and $X^1$ and $X^2$ may be glucose or maltose. Preferably, in Formula 1 or 2, a compound in which each of $R^1$ and $R^2$ may be independently a substituted or unsubstituted $C_3$ to $C_{30}$ alkyl group; and $X^1$ and $X^2$ may be maltose, the compound being referred to as a "norbornene-based maltoside (NBM)."

In one embodiment of the present invention, a compound represented by Formula 1 in which $R^1$ and $R^2$ are $C_9$ alkyl groups; and $X^1$ and $X^2$ are maltose, and which is an exo-diastereomer, is referred to as "X-NBM-C9." Therefore, the compound may be a compound represented by Formula 3:

[Formula 3]

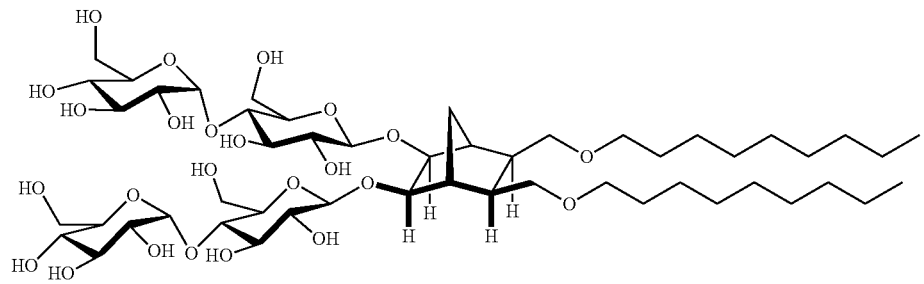

In one embodiment of the present invention, a compound represented by Formula 1 in which $R^1$ and $R^2$ are $C_{10}$ alkyl groups; and $X^1$ and $X^2$ are maltose, and which is an exo-diastereomer, is referred to as "X-NBM-C10." Therefore, the compound may be a compound represented by Formula 4:

[Formula 4]

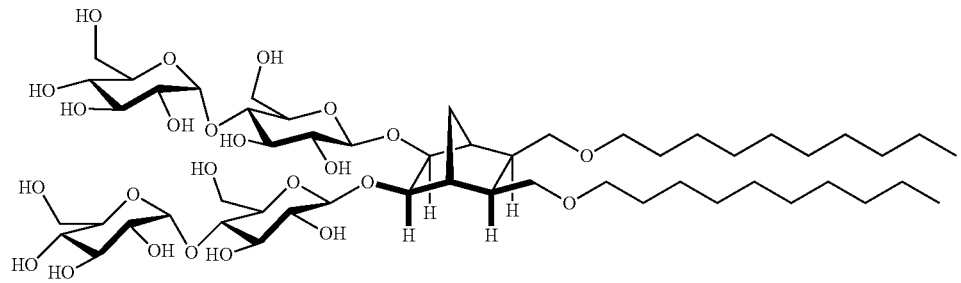

In one embodiment of the present invention, a compound represented by Formula 1 in which $R^1$ and $R^2$ are $C_{11}$ alkyl groups; and $X^1$ and $X^2$ are maltose, and which is an exo-diastereomer, is referred to as "X-NBM-C11." Therefore, the compound may be a compound represented by Formula 5 as follows:

[Formula 5]

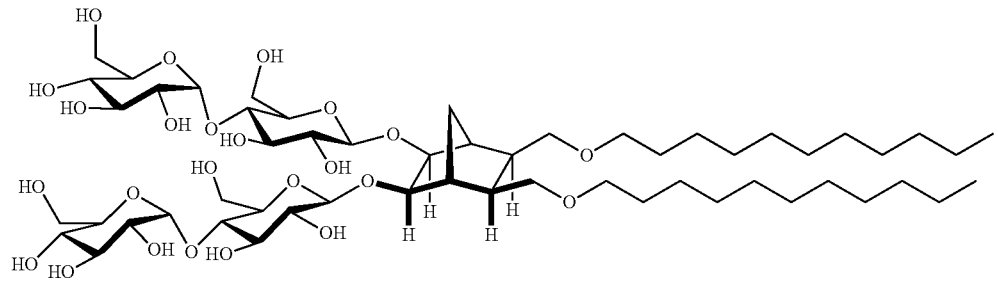

In one embodiment of the present invention, a compound represented by Formula 2 in which $R^1$ and $R^2$ are $C_9$ alkyl groups; and $X^1$ and $X^2$ are maltose, and which is an endo-diastereomer, is referred to as "D-NBM-C9." Therefore, the compound may be a compound represented by Formula 6:

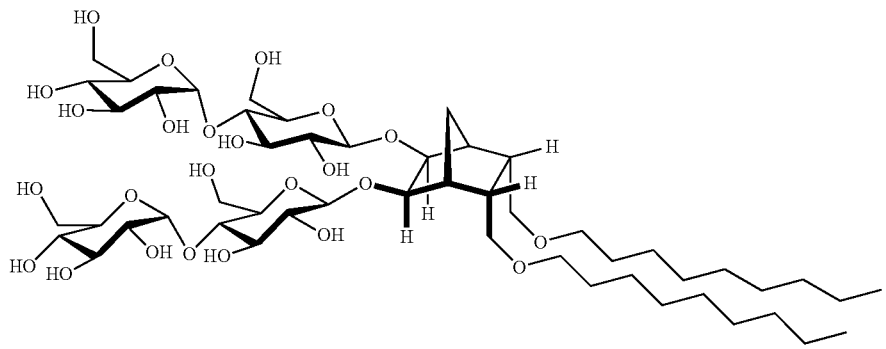

[Formula 6]

In one embodiment of the present invention, a compound represented by Formula 2 in which $R^1$ and $R^2$ are $C_{10}$ alkyl groups; and $X^1$ and $X^2$ are maltose, and which is an endo-diastereomer is referred to as "D-NBM-C10." Therefore, the compound may be a compound represented by Formula 7:

extracting, solubilizing, stabilizing, crystallizing or analyzing a membrane protein, but the present invention is not limited thereto.

Specifically, the extraction may be extraction of a membrane protein from a cell membrane.

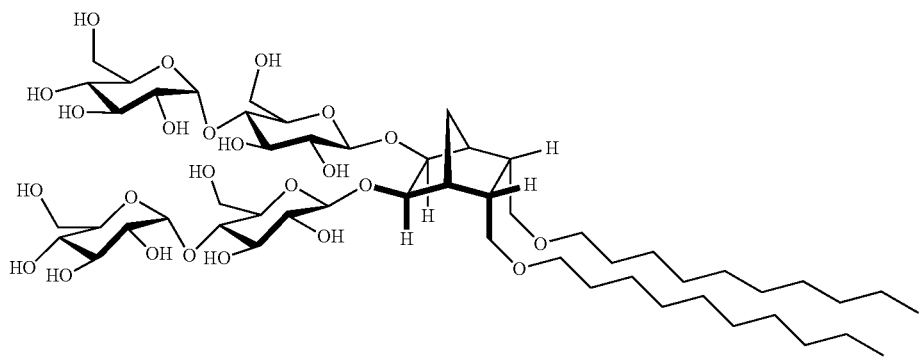

[Formula 7]

In one embodiment of the present invention, a compound represented by Formula 2 in which $R^1$ and $R^2$ are $C_{11}$ alkyl groups; and $X^1$ and $X^2$ are maltose, and which is an endo-diastereomer is referred to as "D-NBM-C11." Therefore, the compound may be a compound represented by Formula 8:

The term "amphiphilic molecule" used herein refers to a molecule that can have an affinity to both of polar and non-polar solvents since there are both of a hydrophobic group and a hydrophilic group in one molecule. The amphiphilic compound or a phospholipid molecule present in cell

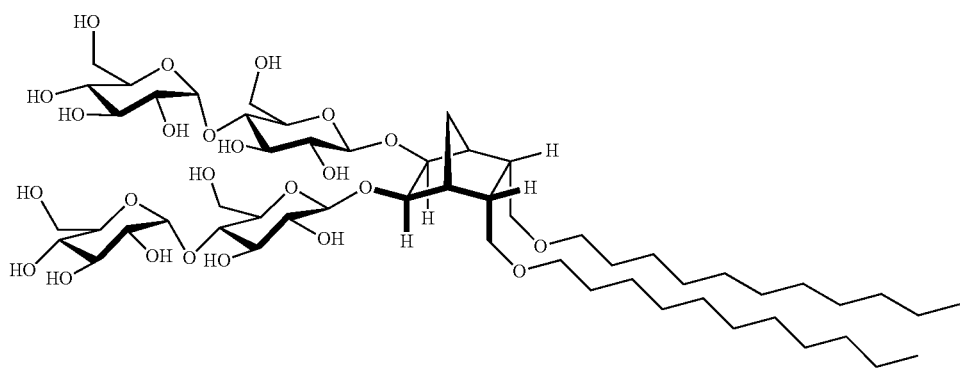

[Formula 8]

The compound according to another embodiment of the present invention may be an amphiphilic molecule for membrane is a molecule having a hydrophilic group and a hydrophobic group at respective ends, has amphiphilicity, and forms a micelle or liposome in an aqueous solution. Since the hydrophilic group is polar, but also has a non-polar group, such an amphiphilic molecule tends to be insoluble in an aqueous solution. However, when a concentration reaches a certain limit concentration (critical micelle concentration, CMC) or more, the hydrophobic groups are gathered inside due to hydrophobic interactions, and the hydrophilic groups are exposed to the surface of the compound, thereby generating a round or oval-shaped micelle, and thus the solubility in water greatly increases.

A method for measuring CMC is not particularly limited, and a method widely known in the art may be used, for example, by fluorescence staining with diphenylhexatriene (DPH).

The compound according to one embodiment of the present invention may have a CMC in an aqueous solution of 0.0001 to 1 mM, specifically, 0.0001 to 0.1 mM, more specifically, 0.001 to 0.1 mM, further more specifically, 0.001 to 0.05 mM, or for example, 0.005 to 0.05 mM, but the present invention is not limited thereto.

While DDM mainly used in conventional membrane protein research has a CMC of 0.17 mM, NBMs of the embodiment have a very small CMC value. Therefore, since NBMs easily form a micelle at a low concentration, they may be used at a small amount to effectively study and analyze membrane proteins, and may be more advantageous than DDM in terms of utilization.

In still another embodiment of the present invention, a composition for extracting, solubilizing, stabilizing, crystallizing or analyzing a membrane protein, which includes the above-described compound, is provided.

Specifically, the extraction may be extraction of membrane proteins from a cell membrane.

The composition may be prepared in the form of micelles, liposomes, emulsion or nanoparticles, but the present invention is not limited thereto.

The micelle may have a radius of 2.0 nm to 30 nm, specifically, 2.0 nm to 20.0 nm, or for example, 3.0 nm to 17.5 nm, but the present invention is not limited thereto.

A method for measuring the radius of a micelle is not particularly limited, and a method well known in the art may be used, and for example, the radius thereof may be measured using a dynamic light scattering (DLS) experiment.

The micelles, liposomes, emulsion or nanoparticles may be bound to membrane proteins due to its internal hydrophobicity. That is, the membrane proteins present in the cell membrane may be extracted and surrounded by the micelles, liposomes, emulsion or nanoparticles. Therefore, the membrane proteins are able to be extracted from the cell membrane, solubilized, stabilized, crystallized or analyzed by the micelle.

The composition may further include a buffer or the like that can help in extracting, solubilizing, stabilizing, crystallizing or analyzing a membrane protein.

In yet another embodiment of the present invention, a method for preparing a compound represented by Formula 1 or 2 below, the method including operations 1) to 4):

1) introducing analkyl group through dialkylation of 5-norbornene-2-exo, 3-exo-dimethanol or 5-norbornene-2-endo, 3-endo-dimethanol as a diastereomer thereof;

2) converting a double bond in norbornene into a diol through dihydroxylation of the product obtained in operation 1);

3) introducing a saccharide with a protective group through glycosylation of the product obtained in operation 2); and 4) performing deprotection of the product obtained in operation 3):

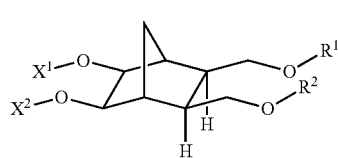

[Formula 1]

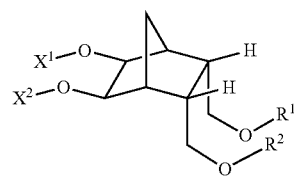

[Formula 2]

In Formula 1 or 2, each of $R^1$ and $R^2$ is independently a substituted or unsubstituted C3 to C30 alkyl group, substituted or unsubstituted $C_3$ to $C_{30}$ cycloalkyl group, or substituted or unsubstituted $C_3$ to $C_{30}$ aryl group; and $X^1$ and $X^2$ are saccharides.

Specifically, each of $R^1$ and $R^2$ may be independently a substituted or unsubstituted $C_3$ to $C_{30}$ alkyl group; and $X^1$ and $X^2$ may be glucose or maltose. Preferably, $X^1$ and $X^2$ may be maltose.

In the operation 2), the dihydroxylation may be Upjohn dihydroxylation. The "Upjohn dihydroxylation" is a reaction that converts alkene into a cis vicinal diol, and may not have reaction selectivity two planes of the alkene, thereby producing two types of isomers. However, in the case of the reaction product, only one isomer is selectively obtained due to a difference in steric hindrance between the two planes. A specific reaction method is well known to the art.

The compound synthesized by the method may be one of compounds of Formulas 3 to 8 according to one embodiment of the present invention, but the present invention is not limited thereto.

In the embodiment, the compound may be synthesized by a simple method performed through four-step short synthesizing operations, and can be mass-produced to study membrane proteins.

In yet another embodiment of the present invention, a method for extracting, solubilizing, stabilizing, crystallizing or analyzing a membrane protein is provided. Specifically, provided is a method for extracting, solubilizing, stabilizing, crystallizing or analyzing a membrane protein, which includes treating a membrane protein with a compound of Formula 1 or 2 in an aqueous solution:

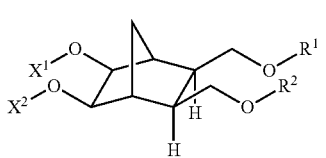

[Formula 1]

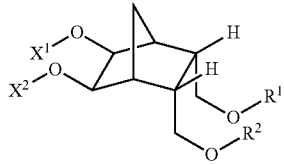

[Formula 2]

In Formula 1 or 2, each of $R^1$ and $R^2$ is independently a substituted or unsubstituted $C_3$ to $C_{30}$ alkyl group, a substituted or unsubstituted $C_3$ to $C_{30}$ cycloalkyl group, or a substituted or unsubstituted $C_3$ to $C_{30}$ aryl group; and $X^1$ and $X^2$ are saccharides.

Specifically, each of $R^1$ and $R^2$ is independently a substituted or unsubstituted $C_3$ to $C_{30}$ alkyl group; and $X^1$ and $X^2$ are glucoses or maltose. Preferably, $X^1$ and $X^2$ are maltose.

The compound may be one of the compounds of Formulas 3 to 8 according to one embodiment of the present invention, but the present invention is not limited thereto.

Specifically, the extraction may be extraction of membrane proteins from a cell membrane.

The term "membrane protein" used in this specification generally refers to a protein or glucoprotein integrated into a lipid bilayer of the cell membrane. The membrane protein is present in various states, for example, passing through the entire layer of a cell membrane or positioned on a surface of the cell membrane, or adhered on the cell membrane, etc. Examples of the membrane protein include enzymes, receptors for peptide hormones and local hormones, acceptable carriers for saccharides, ion channels, cell membrane antigens, etc., but the present invention is not limited thereto.

The membrane proteins include any protein or glycoprotein introduced to the cell membrane lipid bilayer, specifically, uric acid-xanthine/H+ symporter (UapA), leucine transporter (LeuT), human $\beta_2$ adrenergic receptor ($\beta_2$AR), melibiosepermease (MelB$_{st}$), or a combination of two or more thereof, but the present invention is not limited thereto.

The term "extraction of a membrane proteins" used herein refers to separation of membrane proteins from a cell membrane.

The term "solubilization of a membrane proteins" used herein refers to dissolution of water-insoluble membrane proteins in micelles in an aqueous solution.

The term "stabilization of membrane proteins" used herein refers to stable maintenance of tertiary or quaternary structure not to change the structure or function of a membrane protein.

The term "crystallization of a membrane proteins" used herein refers to formation of membrane protein crystals in a solution.

The term "analysis of a membrane protein" used herein refers to analysis of the structure or function of a membrane protein. In the embodiment, the analysis of a membrane protein may be performed by a known method, but the present invention is not limited thereto. For example, the structure of a membrane protein may be analyzed by using electron microscopy or nuclear magnetic resonance.

BRIEF DESCRIPTION OF THE SEVERAL VIEWS OF THE DRAWINGS

The above and other objects, features and advantages of the present invention will become more apparent to those of ordinary skill in the art by describing in detail exemplary embodiments thereof with reference to the accompanying drawings, in which.

Figure 9A:
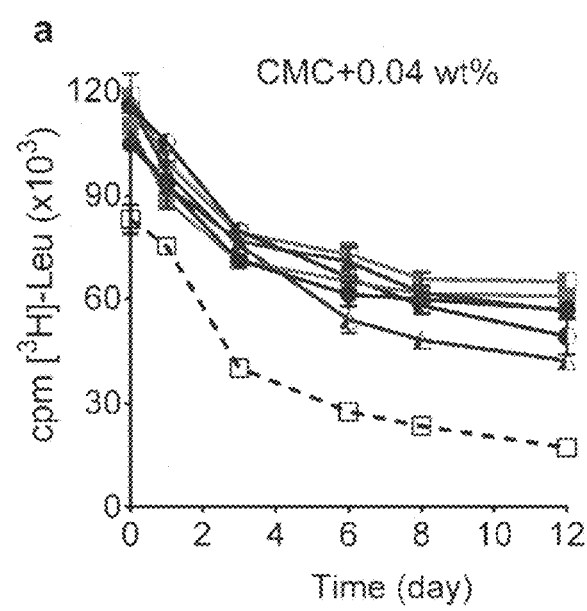
Figure 9B:
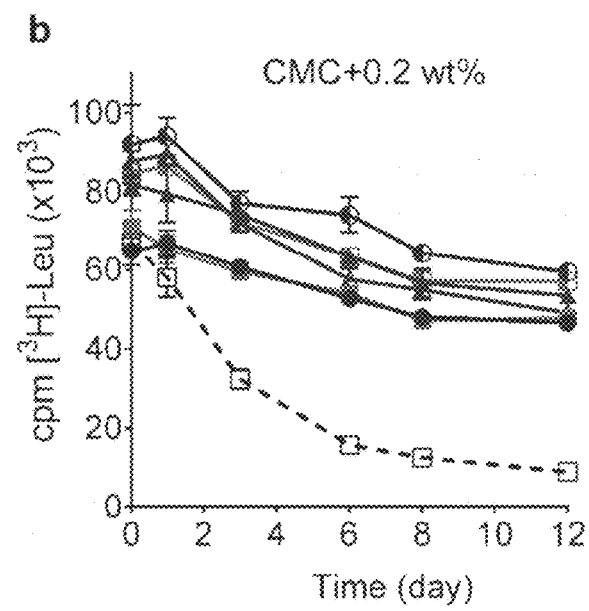
Figure 10:
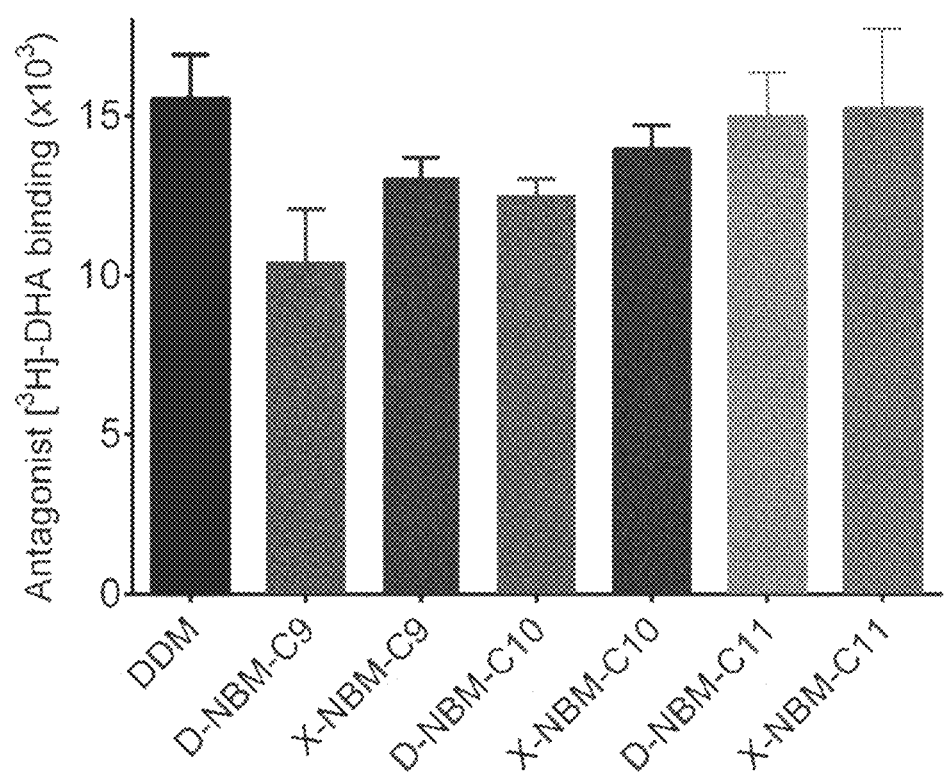
Figure 11A:
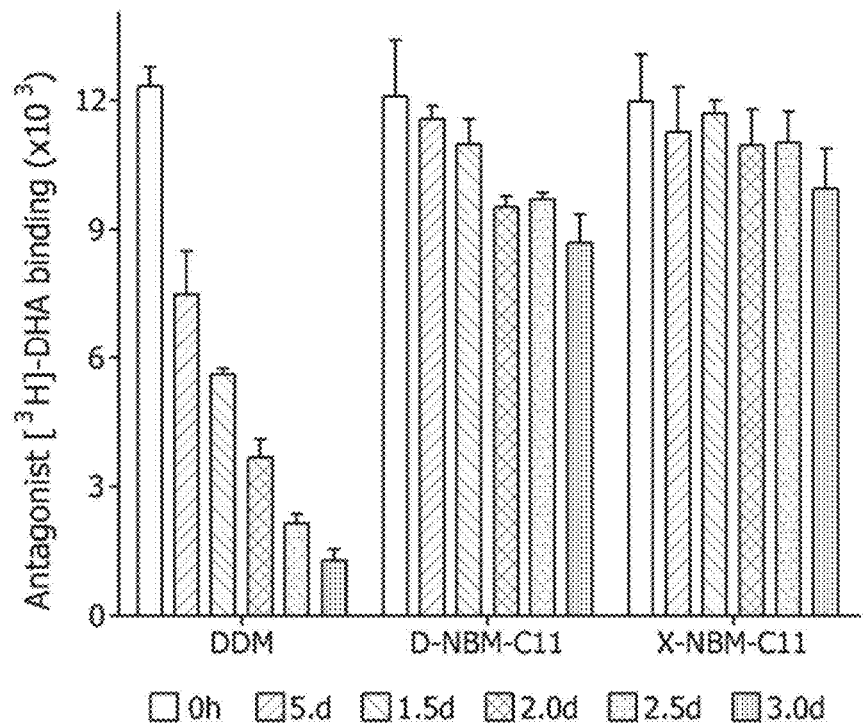
Figure 11B:
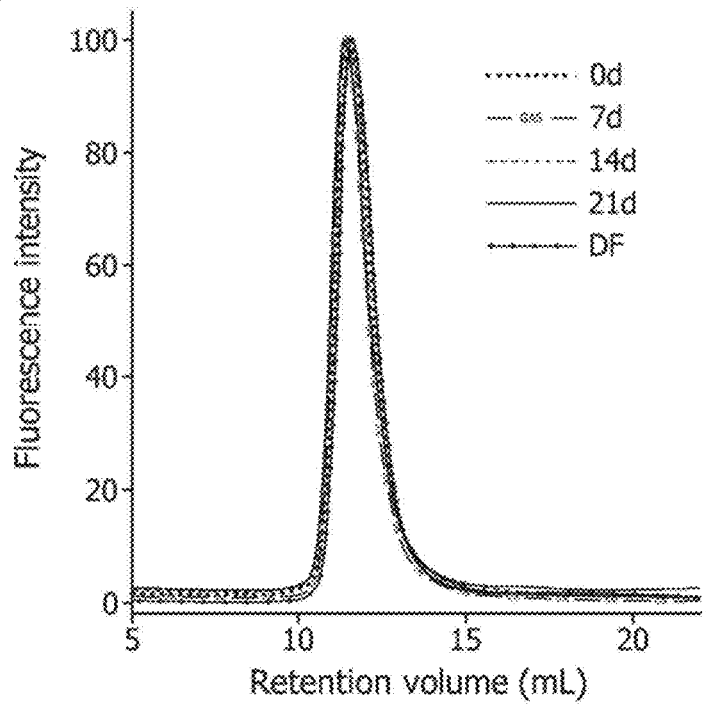
Figure 12A:
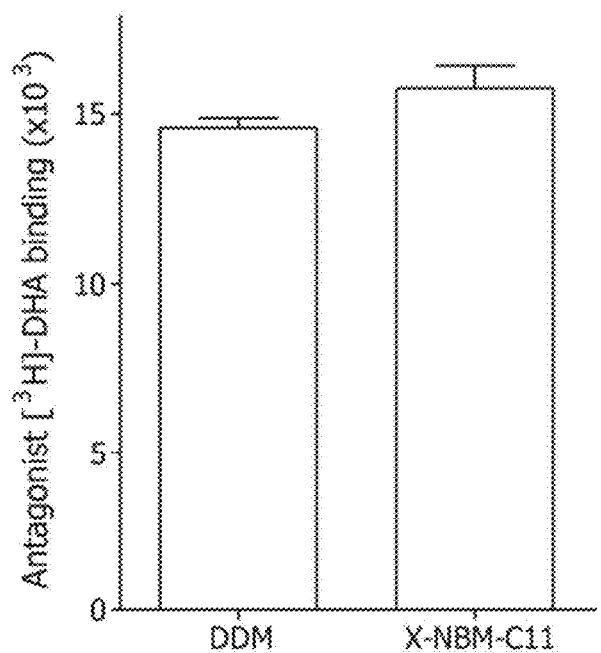
Figure 12B:
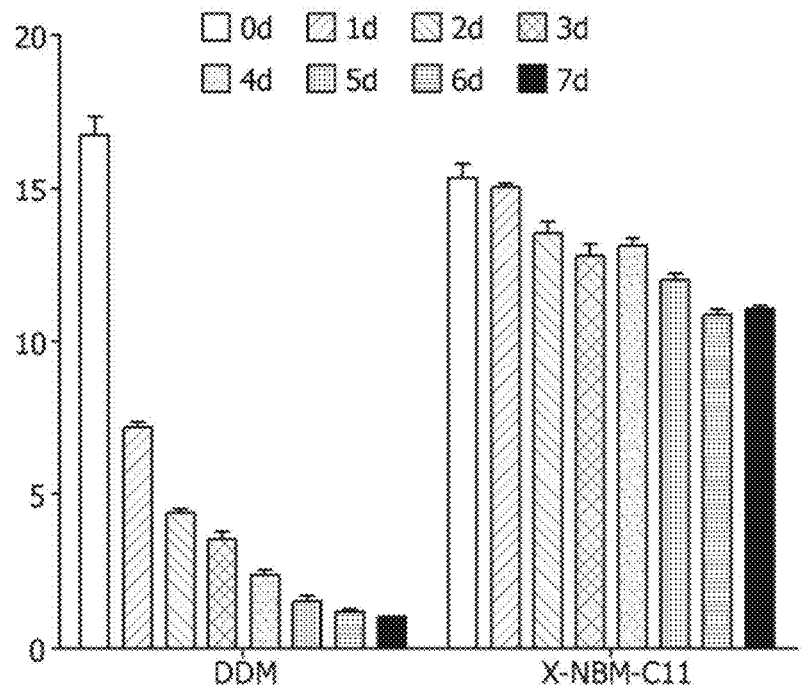
Figure 13:
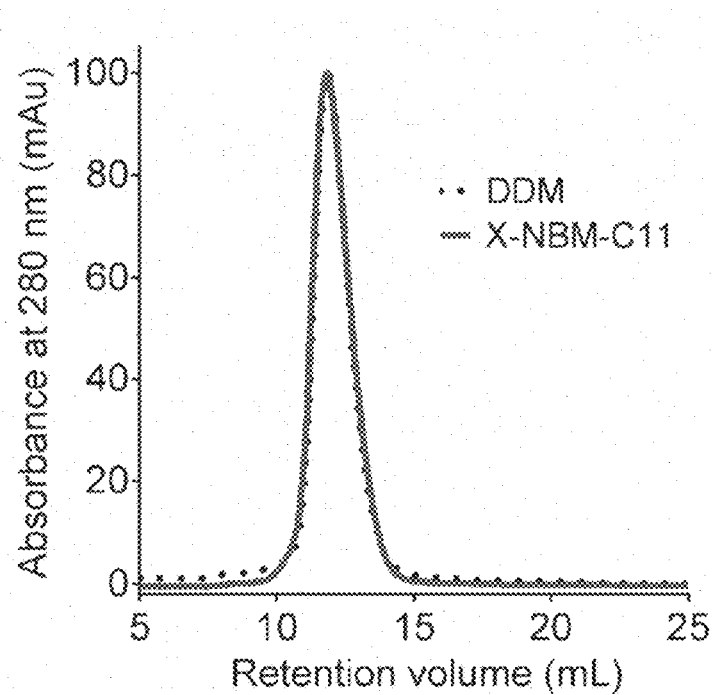
Figure 14:
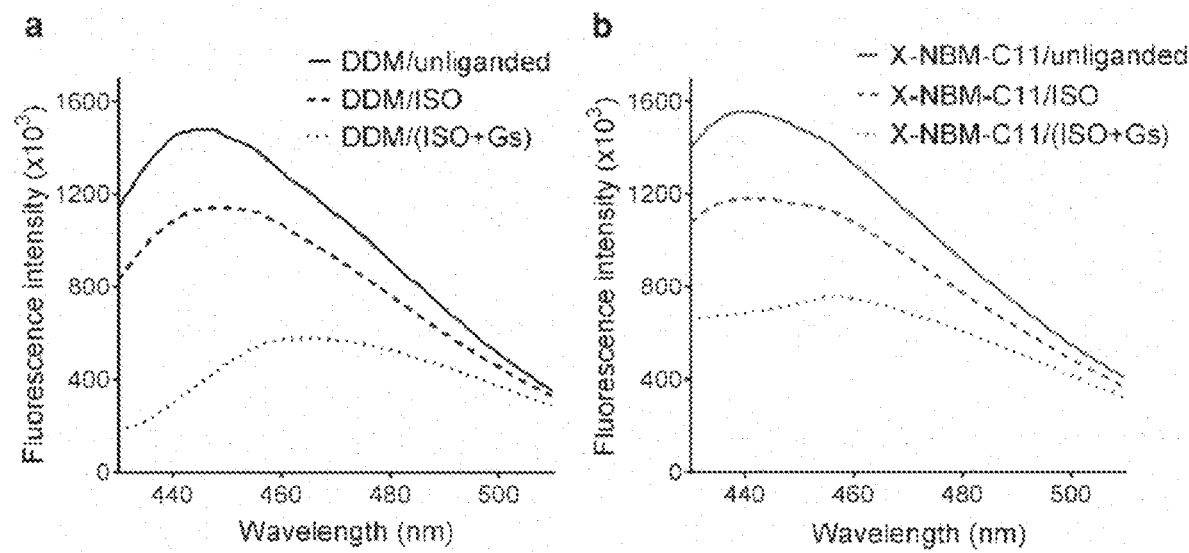
Figure 16:
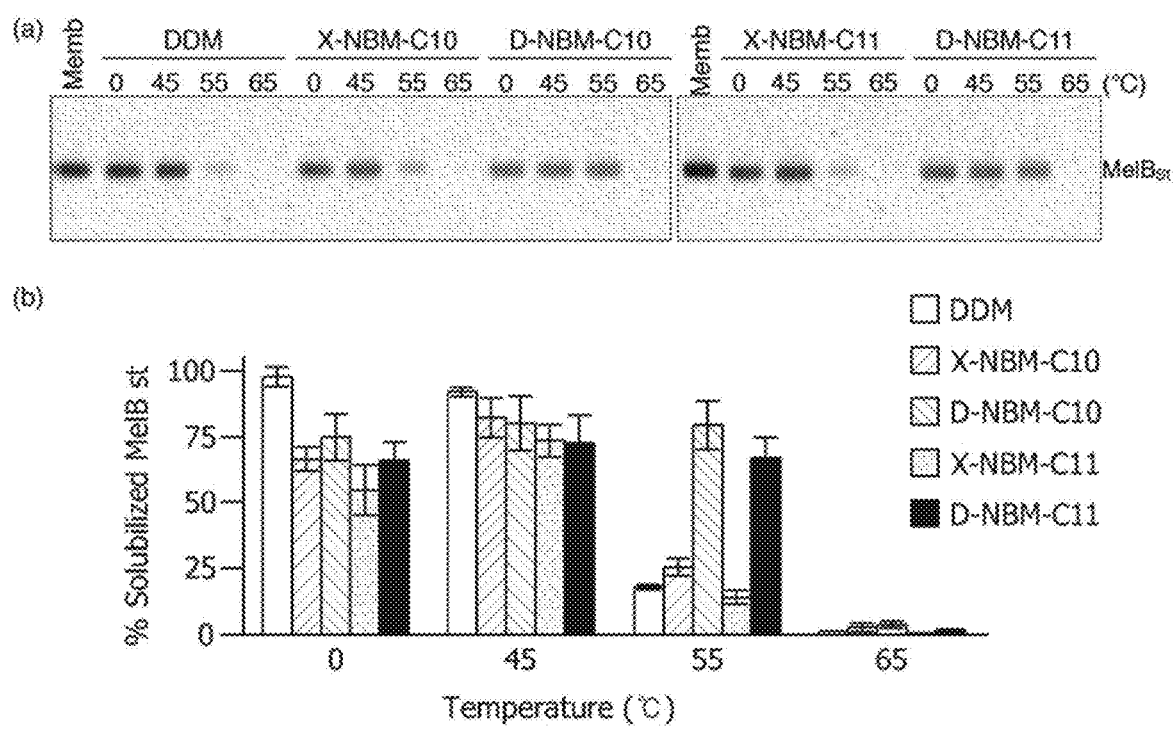

(a) the concentration of X-NBMs, MNG-3 or DDM is CMC+0.2 wt %; and (b) the concentration of D-NBMs, MNG-3 or DDM is CMC+0.2 wt %;

FIGS. 9a and 9b shows the structural stability of a leucine transporter (LeuT) in an aqueous solution with NBMs or DDM. Protein stability was confirmed by measuring the substrate binding activity of the transporter through scintillation proximity assay (SPA). While incubating LeuT in the presence of amphiphilic compounds for 12 days at room temperature, the substrate binding activity of the protein was measured at regular intervals:

(a) the concentration of NBMs or DDM is CMC+0.04 wt %; and (b) the concentration of NBMs or DDM is CMC+0.2 wt %;

(a) the concentration of NBMs or DDM is CMC+0.04 wt %; and (b) the concentration of NBMs or DDM is CMC+0.2 wt %;

FIG. 10 shows the initial ligand binding activity of $\beta_2$AR solubilized by NBMs or DDM, and the ligand binding activity of the protein is measured by a ligand binding assay of [$^3$H]-dihydroalprenolol (DHA);

FIGS. 11a and 11b show the long-term stability of $\beta_2$AR solubilized by NBMs (X-NBM-C11 or D-NBM-C11). (a) the ligand binding activity of the receptor measured at 0 day, 0.5 day, 1.5 day, 2 day, 2.5 day, and 3.0 day, and (b) size exclusion chromatography (SEC) results for NBMs (X-NBM-C11 or D-NBM-C11) and DDM measured at 0 day, 7 day, 14 day, and 21 day to assess the size of a $\beta_2$AR-G protein-binding complex;

FIGS. 12a and 12b show& (a) the comparative initial ligand binding activities of β₂AR extracted from the cell membrane and solubilized by X-NBM-C11 or DDM, and (b) the long-term ligand binding activities of β₂AR extracted from the cell membrane and solubilized by X-NBM-C11 or DDM, monitored at regular intervals for 7 days;

FIG. 13 shows SEC profiles for β₂AR solubilized by X-NBM-C11 or DDM after the exchange of an amphiphilic compound;

FIG. 14 shows fluorescence spectra of a fluorescent substance-labeled receptor (mBBr-β₂AR) solubilized by X-NBM-C11 or DDM. The spectra of mBBr-β2AR are measured in the absence of an agonist, and the presence of an agonist (isoproterenol, ISO) or the combination of an agonist and $G_s$-protein;

FIGS. 15a, 15b, 15c and 15d shows the β₂AR-$G_s$ complex solubilized by X-NBM-C11, monitored by electron microscopy. (a) Entire image, (b) Image obtained by 2D classification assay, (c) Average images of a representative complex in the same direction, and (d) Crystal structure of the β₂AR-$G_s$ complex, showing individual components thereof; and FIG. 16 shows amounts of MelB$_{St}$ proteins solubilized in an aqueous solution after being treated with NBMs or DDM at a concentration of 1.5 wt %, extracted at each of four temperatures (0, 45, 55, or 65° C.), and incubated at the same temperature for 90 minutes:

(a) SDS-PAGE and western blotting result for detecting the amounts of MelB$_{St}$ proteins extracted using individual amphiphilic compounds; and (b) Histogram of the amounts of MelB$_{St}$ proteins extracted using individual amphiphilic compounds, expressed as percentages (%) of the total amount of protein in a membrane sample (Memb) untreated with an amphiphilic compound.

DESCRIPTION OF SPECIFIC EMBODIMENTS OF THE INVENTION

The present invention will be described in further detail with reference to examples below. However, the following examples are merely provided to illustrate the present invention, but not to limit the scope of the present invention. It should be construed that the details which can be easily deduced from the detailed description and examples of the present invention by those of ordinary skill in the art belong to the scope of the present invention.

EXAMPLE 1

Synthesis of NBMs

Figure 1:
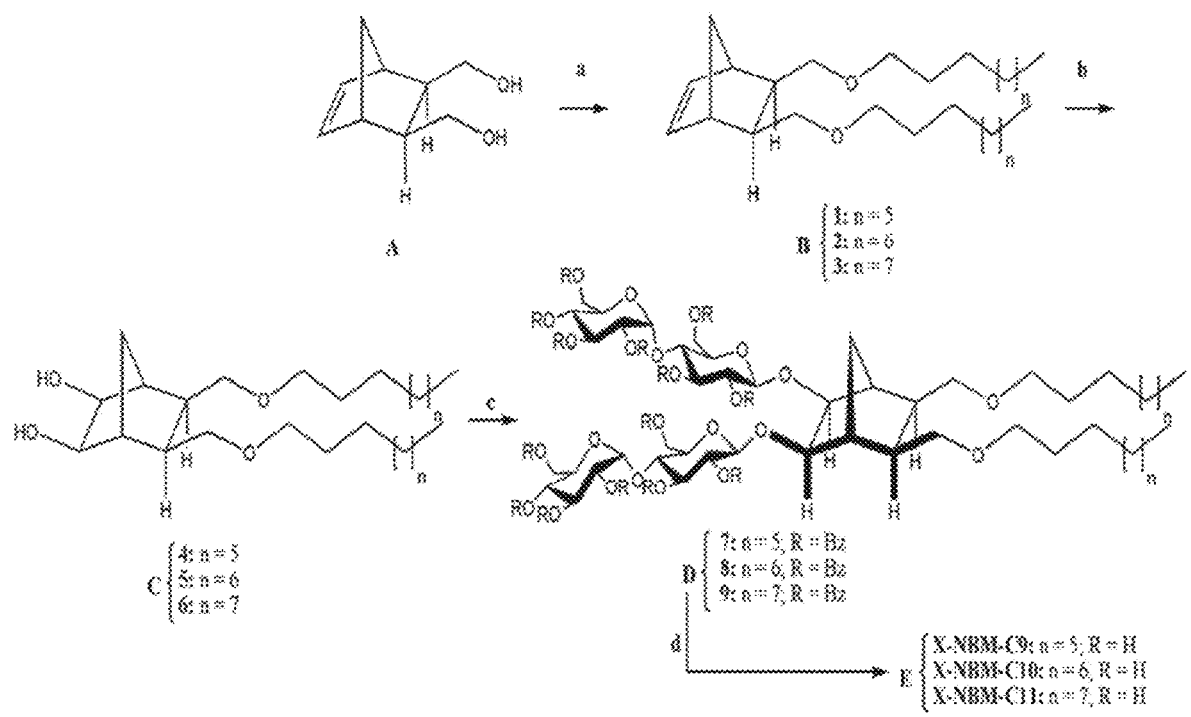
FIG. 1 shows a synthetic scheme of X-NBMs according to Example 1 of the present invention.
Figure 2:
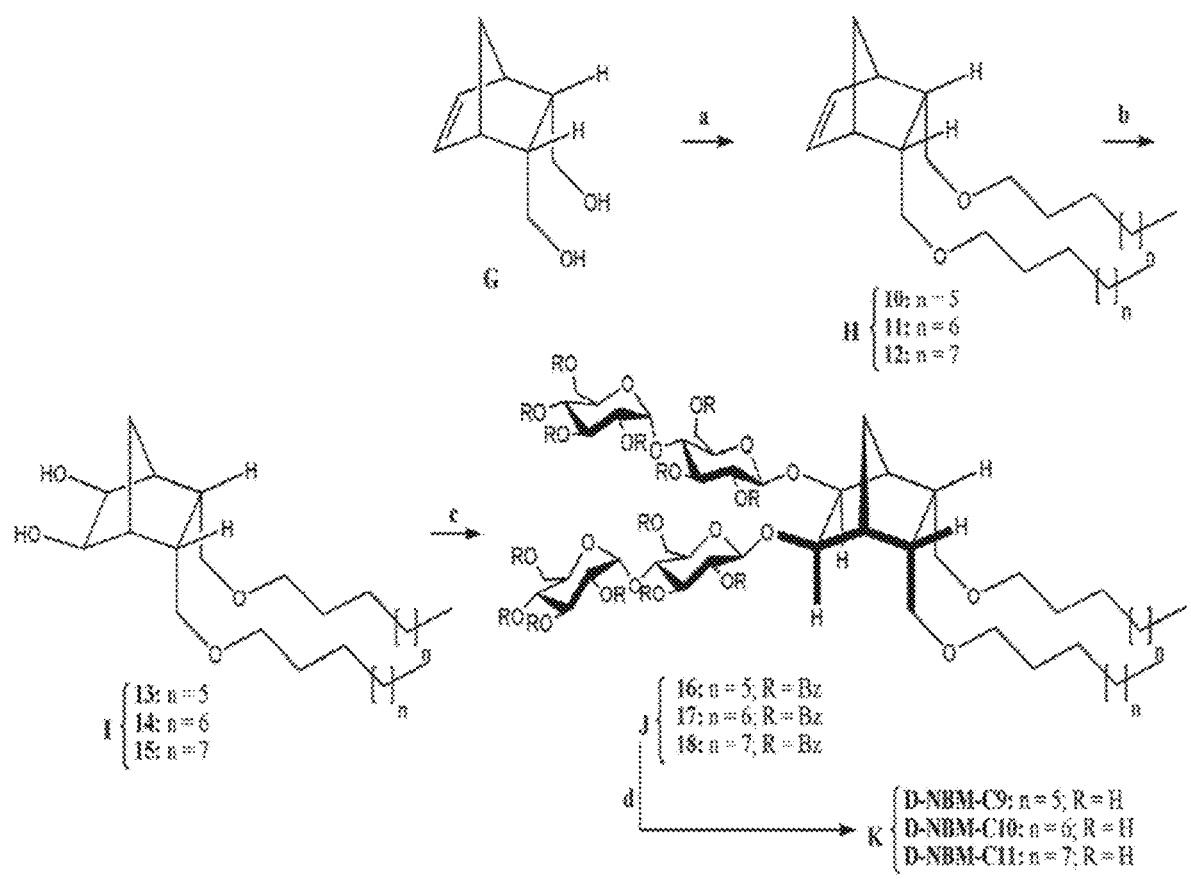
FIG. 2 shows a synthetic scheme of D-NBMs according to Example 2 of the present invention.

The synthetic scheme for X-NBMs or D-NBMs is shown in FIG. 1 or 2. According to the synthetic methods shown in <1-1> to <1-4>, a total of 6 types of compounds including 3 types of each of X-NBMs and D-NBMs were synthesized.

<1-1> General Synthetic Procedures of Dialkylation (Operation a Shown in FIGS. 1 and 2)

Compound A or G (1 equivalent (eq.) 500 mg) and NaH (3.0 eq.) were dissolved in DMF (15 mL) at 0° C. Alkyl iodide (2.9 eq.) was slowly added, and the resulting solution was stirred at 70° C. for 3 days. After the reaction was completed (the reaction completion was confirmed by TLC), the solution was diluted with diethylether (150 mL), and sequentially washed with a 1M HCl aqueous solution (2×20 mL) and brine (100 mL). An organic layer was dried with anhydrous Na₂SO₄, and a solvent was removed using a rotary evaporator. A residue was purified by silica gel column chromatography (EtOAc/hexane), thereby obtaining liquid compound B or H.

<1-2> General Synthesis Procedures of Upjohn Dihydroxylation (Operation b Shown in FIGS. 1 and 2)

An NMO (1.5 eq.) solution in water (50 wt %) was added to a mixture of THF and water (15 mL of 9:1 mixture) at 0° C. Subsequently, the compounds B and H (500 mg, 1.5 eq.) were added at once, the mixture was stirred for 15 minutes, and then OsO₄ (1.4 mL of 2.5 wt % solution in t-BuOH) was slowly added using a syringe for 20 minutes. The resulting mixture was stirred at room temperature for 5 days. The reaction was stopped by adding sodium sulfite (8.0 g), and diluted with water (30 mL). Afterward, the solution was extracted with EtOAc (2×70 mL). The combined organic extracts were dried with anhydrous Na₂SO₄ and vacuum-concentrated, and a residue was purified by silica gel column chromatography (EtOAc/hexane), thereby obtaining orange gum diol C or I.

<1-3> General Synthetic Procedures of Glycosylation (Operation c Shown in FIGS. 1 and 2)

In this method, the synthesis method suggested by Chae, P. S. et al. (J. Am. Chem. Soc. 2016, 138, 3789-3796) was used with a little modification. A mixture of compound C or I (1 eq., 250 mg), AgOTf (2.4 eq.) and collidine (1.0 eq.) in anhydrous CH₂Cl₂ (40 mL) was stirred at −45° C. A solution of 2.4 equivalent perbenzoylated maltosylbromide (synthesized from D-(+)-maltose monohydrate) in CH₂Cl₂ (10 mL) was slowly added to the suspension for 0.5 hours. Following stirring at −45° C. for 0.5 hours, the reaction mixture was heated to 0° C. and stirred for 1 hour. After the reaction was completed, pyridine was added to the reaction mixture, and diluted with CH₂Cl₂ (40 mL) before filtered with celite. The filtered solution was sequentially washed a 1M Na₂S₂O₃ aqueous solution (40 mL), a 0.1 M HCl aqueous solution (40 mL) and brine (2×40 mL). An organic layer was dried with anhydrous Na₂SO₄, and a solvent was removed using a rotary evaporator. A residue was purified by silica gel column chromatography (EtOAc/hexane), thereby obtaining a white solid compound D or J.

<1-4> General Synthetic Procedures of Deprotection Reaction (Operation g Shown in FIG. 1)

In this method, de-O-benzoylation was performed under Zemplen's conditions (Ashton, P. R.; Boyd, S. E.; Brown, C. L.; Jayaraman, N.; Nepogodiev, S. A.; Stoddart, J. F. Chem.-Eur. J. 1996, 2, 1115-1128). An O-protected compound D or J was dissolved in anhydrous MeOH, a 0.5M methanolic solution, NaOMe, was added to the reaction mixture to have a final concentration of 0.05M. The reaction mixture was stirred at room temperature for 14 hours, and neutralized using an Amberlite IR-120 (H⁺ form) resin. The resulting solution was filtrated to remove a resin and washed with MeOH, and the solvent was removed from the filtrate under vacuum conditions (in vacuo). A residue was recrystallized using CH₂Cl₂/MeOH/diethylether, thereby obtaining a white solid compound E or K from which a protective group is completely removed.

PREPARATION EXAMPLE 1

Synthesis of X-NBM-C9

<1-1> Synthesis of Compound B1

According to the general synthetic procedures of dialkylation described in Example 1-1, compound B1 was synthesized with a yield of 82%: ¹H NMR (400 MHz, CDCl₃): δ6.15 (t, J=4.2 Hz, 2H), 3.57 (dd, J=8.0 Hz, 4.0 Hz, 2H), 3.44-3.34 (m, 4H), 3.27 (app. t, J=8.2 Hz, 2H), 2.75 (t, J=4.1 Hz, 2H), 1.77-1.75 (m, 2H), 1.59-1.55 (m, 4H), 1.48 (d, J=8.1 Hz, 1H), 1.40-1.30 (m, 27H), 0.88 (t, J=8.6 Hz, 6H); $^{13}$C NMR (100 MHz, CDCl$_3$): δ137.5, 72.3, 71.4, 45.0, 42.9, 40.7, 30.0, 29.8, 29.7, 29.5, 26.5, 22.9, 14.3.

<1-2> Synthesis of Compound C4

According to the general synthetic procedures of Upjohn dihydroxylation described in Example 1-2, compound C4 was synthesized with a yield of 90%: $^1$H NMR (400 MHz, CDCl$_3$): δ 3.71 (br s, 2H), 3.51 (br s, 2H), 3.42 (dd, J=8.0 Hz, 4.0 Hz, 2H), 3.37-3.32 (m, 4H), 3.22 (app. t, J=7.7 Hz, 2H), 2.09 (br s, 2H), 1.75-1.73 (m, 2H), 1.61 (d, J=8 Hz, 1H), 1.54-1.49 (m, 4H), 1.40-1.20 (m, 27H), 0.86 (t, J=8.1 Hz, 6H); $^{13}$C NMR (100 MHz, CDCl$_3$): δ 74.3, 71.4, 70.3, 46.9, 40.6, 32.1, 29.8 (2C), 29.7, 29.5, 27.5, 26.4, 22.9, 14.3.

<1-3> Synthesis of Compound D7

According to the general synthetic procedures of glycosylation described in Example 1-3, compound D7 was synthesized with a yield of 80%: $^1$H NMR (400 MHz, CDCl$_3$): δ 8.12-7.78 (m, 9H), 7.71-7.50 (m, 14H), 7.42-7.12 (m, 43H), 6.12 (t, J=7.7 Hz, 1H), 6.09 (t, J=7.6 Hz, 1H), 5.79-5.55 (m, 5H), 5.54-5.48 (m, 2H), 5.39-5.33 (m, 3H), 5.03 (br s, 1H), 4.84-4.75 (m, 2H), 4.61-4.25 (m, 10H), 4.11-3.79 (m, 3H), 3.41-3.39 (m, 1H), 3.25-3.16 (m, 4H), 3.06-3.00 (m, 2H), 2.00-1.98 (m, 2H), 1.58-1.39 (m, 5H), 1.38-1.20 (m, 21H), 1.00-1.11 (m, 1H), 0.87 (t, J=7.8 Hz, 6H); $^{13}$C NMR (100 MHz, CDCl$_3$): δ 166.2, 165.9, 165.8, 165.7, 165.6, 165.4, 165.1, 164.9, 164.7, 164.3, 133.4, 133.1, 130.0, 129.9, 129.8, 129.7, 129.6, 129.5 (2C), 129.0, 128.9 (2C), 128.8 (2C), 128.7, 128.6, 128.5 (2C), 128.4, 128.2 (2C), 128.1, 128.0, 99.0, 98.1, 96.9, 96.4, 81.0, 79.2, 72.4, 71.3, 71.0 (2C), 69.2, 69.1, 69.0, 64.1, 62.6, 60.4, 31.9, 29.8, 29.7, 29.6 (2C), 29.5, 29.4 (2C), 26.3, 26.2, 22.8, 22.7, 21.1, 14.2 (2C).

<1-4> Synthesis of X-NBM-C9

According to the general synthetic procedures of deprotection described in Example 1-4, X-NBM-C9 was synthesized with a yield of 95%: $^1$H NMR (400 MHz, CD$_3$OD): δ5.16 (dd, J=12.0 Hz, 4.0 Hz, 2H), 4.57 (d, J=8.0 Hz, 1H), 4.42 (d, J=8.0 Hz, 1H), 4.03-3.99 (m, 2H), 3.93-3.78 (m, 7H), 3.67-3.59 (m, 10H), 3.54-3.22 (m, 24H), 2.27 (br s, 1H), 2.19 (br s, 1H), 1.85-1.74 (m, 3H), 1.55 (app. t, J=8.0 Hz, 4H), 1.45 (d, J=12.0 Hz, 1H), 1.40-1.22 (m, 26H), 0.90 (t, J=8.0 Hz, 6H); $^{13}$C NMR (100 MHz, CD$_3$OD): δ103.4, 103.3, 103.0, 82.8, 82.1, 81.5, 81.3, 77.9, 77.7, 76.9, 76.7, 75.4, 75.2, 74.9, 74.2 (2C), 72.3, 72.2, 71.5, 62.8, 62.4, 47.5, 45.4, 42.1, 41.8, 33.2, 30.9 (2C), 30.7, 30.6, 27.6, 27.5, 23.9, 14.6; HRMS (EI): calcd. for C$_{51}$H$_{92}$O$_{24}$Na+ [M+Na]+ 1111.5876, found 1111.5873.

PREPARATION EXAMPLE 2

Synthesis of X-NBM-C10

<2-1> Synthesis of Compound B2

According to the general synthetic procedures of dialkylation described in Example 1-1, compound B2 was synthesized with a yield of 78%. $^1$H NMR (400 MHz, CDCl$_3$): δ 6.15 (t, J=4.5 Hz, 2H), 3.55 (dd, J=8.0 Hz, 4.0 Hz, 2H), 3.40-3.30 (m, 4H), 3.27 (app. t, J=8.6 Hz, 2H), 2.74 (t, J=4.1 Hz, 2H), 1.77-1.75 (m, 2H), 1.59-1.55 (m, 4H), 1.47 (d, J=8.2 Hz, 1H), 1.40-1.28 (m, 30H), 0.89 (t, J=7.8 Hz, 6H); $^{13}$C NMR (100 MHz, CDCl$_3$): δ 137.5, 72.3, 71.4, 45.1, 42.9, 40.7, 32.1, 30.0, 29.9, 29.8, 29.7, 29.6, 26.5, 22.9, 14.3.

<2-2> Synthesis of Compound C5

According to the general synthetic procedures of Upjohn dihydroxylation described in Example 1-2, compound C5 was synthesized with a yield of 95%: $^1$H NMR (400 MHz, CDCl$_3$): δ 3.89 (br s, 2H), 3.67 (br s, 2H), 3.39 (dd, J=8.0 Hz, 4.1 Hz, 2H), 3.37-3.31 (m, 4H), 3.20 (app. t, J=7.7 Hz, 2H), 2.06 (br s, 2H), 1.72-1.68 (m, 2H), 1.55 (d, J=8.1 Hz, 1H), 1.51-1.48 (m, 4H), 1.35-1.25 (m, 31H), 0.84 (t, J=8.2 Hz, 6H); $^{13}$C NMR (100 MHz, CDCl$_3$): δ 74.1, 71.4, 70.3, 46.8, 40.5, 32.0, 29.8, 29.7, 29.6, 29.5, 27.5, 26.4, 22.8, 14.2.

<2-3> Synthesis of Compound D8

According to the general synthetic procedures of glycosylation described in Example 1-3, compound D8 was synthesized with a yield of 85%: $^1$H NMR (400 MHz, CDCl$_3$): δ 8.10-7.77 (m, 9H), 7.75-7.43 (m, 14H), 7.42-7.17 (m, 40H), 6.18 (t, J=8.0 Hz, 1H), 6.08 (t, J=7.8 Hz, 1H), 5.75-5.64 (m, 5H), 5.51-5.44 (m, 2H), 5.36-5.32 (m, 3H), 5.99 (br s, 1H), 4.80-4.70 (m, 2H), 4.60-4.18 (m, 10H), 3.84-3.53 (m, 3H), 3.40-3.34 (m, 1H), 3.23-3.13 (m, 4H), 3.04-2.97 (m, 2H), 1.96-1.95 (m, 2H), 1.55-1.47 (m, 5H), 1.40-1.20 (m, 22H), 1.05-0.95 (m, 1H), 0.89 (t, J=7.7 Hz, 6H); $^{13}$C NMR (100 MHz, CDCl$_3$): δ 166.3 (2C), 166.0 165.9, 165.8, 165.7, 165.5, 165.4, 165.2, 165.0, 164.8, 164.4, 133.5 (2C), 133.4, 133.2, 130.2, 130.1, 130.0 (2C), 129.9 (2C), 129.8, 129.7 (2C), 129.6, 129.1, 128.9 (2C), 128.7, 128.6, 128.5 (2C), 128.4, 128.3, 128.2, 128.1, 99.9, 98.2, 96.9, 96.8, 81.2, 78.9, 71.4, 71.2, 70.7, 70.3, 70.1, 69.3, 69.2, 69.1, 64.2, 62.7, 40.3, 32.1 (2C), 29.9, 29.8 (2C), 29.7 (2C), 29.5, 26.5, 26.3, 22.9, 22.8, 14.3 (2C).

<2-4> Synthesis of X-NBM-C10

According to the general synthetic procedures of deprotection described in Example 1-4, X-NBM-C10 was synthesized with a yield of 89%: $^1$H NMR (400 MHz, CD$_3$OD): δ5.15 (dd, J=12.0 Hz, 4.0 Hz, 2H), 4.57 (d, J=8.0 Hz, 1H), 4.43 (d, J=8.0 Hz, 1H), 4.03-3.98 (m, 2H), 3.92-3.81 (m, 7H), 3.65-3.59 (m, 10H), 3.53-3.22 (m, 29H), 2.27 (br s, 1H), 2.20 (br s, 1H), 1.84-1.74 (m, 3H), 1.55 (app. t, J=8.0 Hz, 4H), 1.46 (d, J=12.0 Hz, 1H), 1.40-1.22 (m, 31H), 0.90 (t, J=8.0 Hz, 6H); $^{13}$C NMR (100 MHz, CD$_3$OD): δ103.5, 103.2, 103.0, 82.9, 82.5, 81.8, 81.6, 81.4, 81.3, 77.8, 77.7, 76.9, 76.7, 76.6, 75.2, 75.0, 74.9, 74.1, 72.2, 71.6, 71.5, 62.7, 62.1, 47.5, 45.4, 42.0, 41.8, 33.2, 30.9 (3C), 30.7, 30.6, 29.7, 27.5 (2C), 23.9, 14.6; HRMS (EI): calcd. for C$_{53}$H$_{96}$O$_{24}$Na+ [M+Na]+ 1139.6189, found 1139.6187.

PREPARATION EXAMPLE 3

Synthesis of X-NBM-C11

<3-1> Synthesis of Compound B3

According to the general synthetic procedures of dialkylation described in Example 1-1, compound B3 was synthesized with a yield of 83%: $^1$H NMR (400 MHz, CDCl$_3$): δ 6.14 (t, J=4.2 Hz, 2H), 3.56 (dd, J=8.0 Hz, 4.0 Hz, 2H), 3.41-3.36 (m, 4H), 3.27 (app. t, J=7.8 Hz, 2H), 2.74 (t, J=4.4 Hz, 2H), 1.77-1.75 (m, 2H), 1.60-1.53 (m, 4H), 1.48 (d, J=8.2 Hz, 1H), 1.40-1.20 (m, 41H), 0.88 (t, J=7.9 Hz, 6H); $^{13}$C NMR (100 MHz, CDCl$_3$): δ 137.5, 72.3, 71.4, 45.0, 42.9, 40.7, 32.1, 30.0, 29.8 (2C), 29.7, 29.6, 29.5 (2C), 26.5, 22.9, 14.3.

<3-2> Synthesis of Compound C6

According to the general synthetic procedures of Upjohn dihydroxylation described in Example 1-2, compound C6 was synthesized with a yield of 91%: $^1$H NMR (400 MHz, CDCl$_3$): δ 3.84 (br s, 2H), 3.71 (br s, 2H), 3.44 (dd, J=8.1 Hz, 4.1 Hz, 2H), 3.40-3.31 (m, 4H), 3.24 (app. t, J=7.8 Hz, 2H), 2.10 (br s, 2H), 1.80-1.70 (m, 2H), 1.62 (d, J=8.0 Hz, 1H), 1.56-1.51 (m, 4H), 1.40-1.20 (m, 34H), 0.88 (t, J=7.9 Hz, 6H); $^{13}$C NMR (100 MHz, CDCl$_3$): δ 74.2, 71.4, 70.3, 46.8, 40.5, 32.1, 29.8, 29.6, 29.5, 27.5, 26.4, 22.8, 14.3.

<3-3> Synthesis of Compound D9

According to the general synthetic procedures of glycosylation described in Example 1-3, compound D9 was synthesized with a yield of 87%: $^1$H NMR (400 MHz, CDCl$_3$): δ 8.09-7.87 (m, 9H), 7.77-7.51 (m, 15H), 7.42-7.14 (m, 48H), 6.16 (t, J=8.1 Hz, 1H), 6.08 (t, J=7.9 Hz, 1H), 5.76-5.61 (m, 5H), 5.51-5.44 (m, 2H), 5.32-5.29 (m, 3H), 5.00 (br s, 1H), 4.83-4.71 (m, 2H), 4.59-4.21 (m, 11H), 3.93-3.71 (m, 3H), 3.40-3.34 (m, 1H), 3.29-3.10 (m, 4H), 3.09-2.95 (m, 2H), 1.97-1.95 (m, 2H), 1.55-1.47 (m, 6H), 1.40-1.20 (m, 33H), 1.02-0.92 (m, 1H), 0.86 (t, J=7.8 Hz, 6H); $^{13}$C NMR (100 MHz, CDCl$_3$): δ 166.3 (2C), 166.1, 165.9, 165.8, 165.7, 165.5, 165.3, 165.2, 165.1, 164.8, 164.4, 133.4, 133.3, 133.2 (2C), 133.0, 130.2, 130.1, 129.9 (2C), 129.8, 129.7, 129.6, 129.2, 129.0, 128.9 (2C), 128.7, 128.6 (2C), 128.5 (2C), 128.4, 128.3, 128.2, 128.1, 99.7, 98.5, 97.3, 97.0, 80.7, 79.6, 71.8, 71.4, 71.2, 70.7, 70.6, 70.3, 70.1, 69.4, 69.3, 69.2, 69.1, 64.2, 62.7, 40.5, 40.3, 32.1 (2C), 29.9, 29.8, 29.7 (2C), 29.6, 29.5, 28.6, 26.4 (2C), 22.9, 14.3.

<3-4> Synthesis of X-NBM-C11

According to the general synthetic procedures of deprotection described in Example 1-4, X-NBM-C10 was synthesized with a yield of 97%: $^1$H NMR (400 MHz, CD$_3$OD): δ5.16 (dd, J=12.0 Hz, 4.0 Hz, 2H), 4.57 (d, J=8.0 Hz, 1H), 4.43 (d, J=8.0 Hz, 1H), 4.03-3.98 (m, 2H), 3.93-3.81 (m, 7H), 3.68-3.58 (m, 9H), 3.53-3.22 (m, 22H), 2.27 (br s, 1H), 2.19 (br s, 1H), 1.84-1.74 (m, 3H), 1.54 (app. t, J=4.0 Hz, 4H), 1.45 (d, J=10.4 Hz, 1H), 1.40-1.22 (m, 35H), 0.90 (t, J=6.4 Hz, 6H); $^{13}$C NMR (100 MHz, CD$_3$OD): δ103.5, 103.3, 103.1, 82.9, 82.2, 81.6, 81.4, 77.9, 77.7, 76.9, 76.8, 75.5, 75.2, 74.9, 74.3, 74.2, 72.3 (2C), 71.6, 62.9, 62.4, 47.5, 45.5, 42.1, 41.9, 33.2, 30.9 (2C), 30.8, 30.7, 29.6, 27.6 (2C), 23.9, 14.6; HRMS (EI): calcd. for C$_{55}$H$_{100}$O$_{24}$Na+ [M+Na]+ 1167.6502, found 1167.6499.

PREPARATION EXAMPLE 4

Synthesis of D-NBM-C9

<4-1> Synthesis of Compound H10

According to the general synthetic procedures of dialkylation described in Example 1-1, compound H was synthesized with a yield of 81%: $^1$H NMR (400 MHz, CDCl$_3$): δ 6.12 (s, 2H), 3.38-3.28 (m, 4H), 3.22 (dd, J=12.0 Hz, 8.0 Hz, 2H), 3.00 (t, J=7.8 Hz, 2H), 2.91 (br s, 2H), 2.45 (br s, 2H) 1.59-1.50 (m, 4H), 1.44 (d, J=7.9 Hz, 1H), 1.39-1.22 (m, 28H), 0.88 (t, J=8.0 Hz, 6H); $^{13}$C NMR (100 MHz, CDCl$_3$): δ 135.5, 71.3, 71.0, 49.2, 45.8, 41.7, 32.1, 30.0, 29.8, 29.7, 29.5, 26.5, 22.9, 14.3.

<4-2> Synthesis of Compound I13

According to the general synthetic procedures of Upjohn dihydroxylation described in Example 1-2, compound I13 was synthesized with a yield of 91%: $^1$H NMR (400 MHz, CDCl$_3$): δ 3.99 (br s, 2H), 3.44 (dd, J=8.0 Hz, 4.0 Hz, 2H), 3.71 (t, J=7.8 Hz, 6H), 3.29 (br s, 2H), 2.25 (br s, 4H), 1.88 (d, J=10.4 Hz, 1H), 1.60-1.51 (m, 4H), 1.33-1.22 (m, 24H), 1.20 (d, J=10.4 Hz, 1H), 0.88 (t, J=8.4 Hz, 6H); $^{13}$C NMR (100 MHz, CDCl$_3$): δ 71.5, 69.5, 68.1, 47.2, 38.7, 33.2, 32.1, 29.9, 29.8, 29.7, 29.5, 26.4, 22.8, 14.3.

<4-3> Synthesis of Compound J16

According to the general synthetic procedures of glycosylation described in Example 1-3, compound J16 was synthesized with a yield of 78%: $^1$H NMR (400 MHz, CDCl$_3$): δ 8.11-8.09 (m, 10H), 7.99-7.68 (m, 14H), 7.52-7.16 (m, 45H), 6.08 (t, J=8.4 Hz, 1H), 6.06 (t, J=7.8 Hz, 1H), 5.77-5.64 (m, 5H), 5.54-5.45 (m, 3H), 5.38-5.31 (m, 2H), 4.96 (br s, 1H), 4.87-4.84 (m, 1H), 4.69-4.44 (m, 9H), 4.33-4.28 (m, 3H), 4.04-3.97 (m, 2H), 3.87-3.78 (m, 2H), 3.49-3.31 (m, 3H), 3.20-3.03 (m, 4H), 2.22 (br s, 1H), 2.18 (br s, 1H), 2.05 (br s, 2H), 1.66-1.58 (m, 3H), 1.43-1.23 (m, 23H), 0.87 (t, J=6.4 Hz, 6H); $^{13}$C NMR (100 MHz, CDCl$_3$): δ 166.2 (2C), 166.0, 165.9, 165.8, 165.7, 165.5, 165.2 (2C), 165.0, 164.7, 164.4, 133.4 (2C), 133.2, 133.1, 133.0, 130.2, 130.1, 130.0, 129.9 (2C), 129.7 (2C), 129.5 (2C), 129.1, 129.0, 128.9 (2C), 128.8, 128.7 (2C), 128.6, 128.5 (2C), 128.3 (2C), 128.2, 128.1, 99.6, 98.7, 97.3, 97.0, 75.3, 75.0, 74.9, 74.3, 73.9, 72.8, 72.5, 71.9, 71.6, 71.3, 71.1, 70.6, 70.2, 70.1, 69.3, 69.2, 69.1, 68.2, 67.5, 64.7, 64.1, 62.7, 62.6, 46.5, 44.7, 38.6, 37.9, 33.9, 32.0, 30.1, 29.8 (3C), 29.6 (2C), 29.4, 26.5, 26.4, 22.8, 14.3 (2C).

<4-4> Synthesis of D-NBM-C9

According to the general synthetic procedures of deprotection described in Example 1-4, D-NBM-C9 was synthesized with a yield of 92%: $^1$H NMR (400 MHz, CD$_3$OD): δ5.08 (t, J=4.8 Hz, 2H), 4.48 (d, J=8.0 Hz, 1H), 4.26 (d, J=8.0 Hz, 1H), 4.16 (br s, 2H), 3.81-3.73 (m, 7H), 3.66-3.43 (m, 12H), 3.37-3.15 (m, 17H), 2.33 (br s, 1H), 2.27 (br s, 1H), 2.15 (br s, 2H), 1.99 (d, J=9.6 Hz, 1H), 1.48 (app. t, J=6.8 Hz, 4H), 1.32-1.12 (m, 26H), 0.82 (app. t, J=5.6 Hz, 6H); $^{13}$C NMR (100 MHz, CD$_3$OD): δ103.8, 103.5, 103.1, 103.0, 81.4, 78.2, 78.0, 77.9, 77.7, 77.0, 76.7, 75.4, 75.2, 74.9, 74.2, 74.1, 72.3 (2C), 71.5, 69.5, 69.1, 62.8, 62.3, 48.0, 45.7, 39.9 (2C), 35.4, 33.2 (2C), 31.0, 30.9, 30.8, 30.7, 30.6, 27.6, 27.5, 23.9, 14.6; HRMS (EI): calcd. for C$_{51}$H$_{92}$O$_{24}$Na+ [M+Na]+ 1111.5876, found 1111.5872.

PREPARATION EXAMPLE 5

Synthesis of D-NBM-C10

<5-1> Synthesis of Compound H11

According to the general synthetic procedures of dialkylation described in Example 1-1, compound H11 was synthesized with a yield of 78%: $^1$H NMR (400 MHz, CDCl$_3$): δ 6.08 (s, 2H), 3.38-3.27 (m, 4H), 3.20 (dd, J=12.0 Hz, 8.0 Hz, 2H), 2.97 (t, J=8.1 Hz, 2H), 2.88 (br s, 2H), 2.42 (br s, 2H), 1.53-1.45 (m, 4H), 1.43 (d, J=8.0 Hz, 1H), 1.38-1.24 (m, 30H), 0.85 (t, J=8.0 Hz, 6H); $^{13}$C NMR (100 MHz, CDCl$_3$): δ 135.4, 71.2, 71.0, 49.2, 45.8, 41.6, 32.1, 29.9, 29.8 (2C), 29.7, 29.5, 26.4, 22.9, 14.3.

<5-2> Synthesis of Compound I14

According to the general synthetic procedures of Upjohn dihydroxylation described in Example 1-2, compound I14 was synthesized with a yield of 94%: $^1$H NMR (400 MHz, CDCl$_3$): δ 3.92 (br s, 2H), 3.65 (br s, 2H), 3.39 (dd, J=8.0 Hz, 4.2 Hz, 2H), 3.32 (t, J=8.0 Hz, 6H), 2.19 (br s, 4H), 1.83 (d, J=12 Hz, 1H), 1.52-1.48 (m, 4H), 1.33-1.17 (m, 30H), 1.14 (d, J=11.7 Hz, 1H), 0.83 (t, J=7.8 Hz, 6H); $^{13}$C NMR (100 MHz, CDCl$_3$): δ 71.4, 69.3, 68.4, 47.1, 38.6, 33.2, 32.1, 29.8 (2C), 29.7, 29.6, 29.5, 26.3, 22.8, 14.2.

<5-3> Synthesis of Compound J17

According to the general synthetic procedures of glycosylation described in Example 1-3, compound J17 was synthesized with a yield of 84%: $^1$H NMR (400 MHz, CDCl$_3$): δ 8.11-8.06 (m, 10H), 7.99-7.70 (m, 15H), 7.51-7.18 (m, 44H), 6.18 (t, J=8.2 Hz, 1H), 6.08 (t, J=7.8 Hz, 1H), 5.78-5.67 (m, 5H), 5.52-5.46 (m, 3H), 5.34-5.31 (m, 2H), 4.97 (br s, 1H), 4.87-4.84 (m, 1H), 4.67-4.44 (m, 9H), 4.33-4.29 (m, 3H), 4.04-3.98 (m, 2H), 3.82-3.78 (m, 2H), 3.49-3.33 (m, 3H), 3.21-3.03 (m, 4H), 2.22 (br s, 1H), 2.18 (br s, 1H), 2.06 (br s, 2H), 1.66-1.60 (m, 2H), 1.44-1.23 (m, 26H), 0.87 (app. t, J=6.4 Hz, 6H); $^{13}$C NMR (100 MHz, CDCl$_3$): δ 166.2 (2C), 166.0, 165.9, 165.8, 165.7, 165.5, 165.2 (2C), 165.0, 164.7, 164.4, 133.4, 133.2, 133.1, 133.0, 130.1, 130.0, 129.9, 129.8, 129.7 (3C), 129.5, 129.4, 129.1, 129.0, 128.9 (2C), 128.8, 128.7 (2C), 128.6, 128.5, 128.3 (2C), 128.2, 128.1, 99.6, 98.6, 97.3, 97.0, 75.4, 75.3, 75.0, 74.9, 74.2, 73.8, 72.8, 72.5, 71.8, 71.6, 71.3, 71.2, 71.1, 70.6, 70.2, 69.3, 69.2 (2C), 69.0, 68.2, 67.5, 64.6, 64.0, 62.7, 62.6, 46.5, 44.7, 38.5, 37.8, 33.9, 32.1, 30.1, 29.9, 29.8, 29.7, 29.6 (2C), 29.5, 26.5, 26.4, 22.8 (2C), 14.3.

<5-4> Synthesis of D-NBM-C10

According to the general synthetic procedures of deprotection described in Example 1-4, D-NBM-C10 was synthesized with a yield of 96%: $^1$H NMR (400 MHz, CD$_3$OD): δ5.15 (t, J=4.0 Hz, 2H), 4.56 (d, J=8.0 Hz, 1H), 4.33 (d, J=8.0 Hz, 1H), 4.24 (br s, 2H), 3.93-3.79 (m, 7H), 3.69-3.53 (m, 13H), 3.45-3.22 (m, 19H), 2.40 (br s, 1H), 2.35 (br s, 1H), 2.22 (br s, 2H), 2.08 (d, J=12.0 Hz, 1H), 1.56 (app. t, J=4.0 Hz, 4H), 1.40-1.20 (m, 30H), 0.90 (t, J=8.0 Hz, 6H); $^{13}$C NMR (100 MHz, CD$_3$OD): δ103.9, 103.6, 103.2, 103.1, 81.5, 78.2, 78.0, 77.9, 77.8, 77.1, 76.8, 75.4, 75.2, 74.9, 74.3, 74.2, 72.4, 72.3, 71.6, 69.5, 69.1, 62.9, 62.4, 48.0, 45.7, 40.0, 39.9, 35.4, 33.2, 31.0 (2C), 30.9, 30.8 (2C), 30.7, 30.6, 27.6 (2C), 23.9, 14.6; HRMS (EI): calcd. for C$_{53}$H$_{96}$O$_{24}$Na+ [M+Na]+ 1139.6189, found 1139.6187.

PREPARATION EXAMPLE 6

Synthesis of D-NBM-C11

<6-1> Synthesis of Compound H12

According to the general synthetic procedures of dialkylation described in Example 1-1, compound H12 was synthesized with a yield of 83%: $^1$H NMR (400 MHz, CDCl$_3$): δ 6.11 (s, 2H), 3.37-3.30 (m, 4H), 3.22 (dd, J=11.8 Hz, 8.0 Hz, 2H), 3.00 (t, J=8.0 Hz, 2H), 2.91 (br s, 2H), 2.45 (br s, 2H), 1.56-1.45 (m, 4H), 1.46 (d, J=12.2 Hz, 1H), 1.38-1.21 (m, 34H), 0.88 (t, J=7.9 Hz, 6H); $^{13}$C NMR (100 MHz, CDCl$_3$): δ 135.4, 71.2, 71.0, 49.2, 45.8, 41.6, 32.1, 29.9, 29.8, 29.7, 29.6, 26.5, 22.9, 14.3.

<6-2> Synthesis of Compound I15

According to the general synthetic procedures of Upjohn dihydroxylation described in Example 1-2, compound I15 was synthesized with a yield of 93%: $^1$H NMR (400 MHz, CDCl$_3$): δ 4.00 (br s, 2H), 3.44 (dd, J=8.2 Hz, 4.1 Hz, 2H), 3.37 (t, J=7.9 Hz, 6H), 3.13 (br s, 2H), 2.26 (br s, 4H), 1.88 (d, J=7.8 Hz, 1H), 1.60-1.53 (m, 4H), 1.39-1.17 (m, 34H), 0.88 (t, J=7.8 Hz, 6H); $^{13}$C NMR (100 MHz, CDCl$_3$): δ 71.5, 69.6, 68.1, 47.3, 38.7, 33.2, 32.1, 29.9, 29.8, 29.7, 29.5, 26.4, 22.9, 14.3.

<6-3> Synthesis of Compound J18

According to the general synthetic procedures of glycosylation described in Example 1-3, compound J18 was synthesized with a yield of 85%: $^1$H NMR (400 MHz, CDCl$_3$): δ 8.11-7.99 (m, 10H), 7.89-7.68 (m, 14H), 7.50-7.16 (m, 46H), 6.15 (t, J=8.1 Hz, 1H), 6.08 (t, J=7.9 Hz, 1H), 5.78-5.67 (m, 5H), 5.51-5.45 (m, 3H), 5.34-5.31 (m, 2H), 4.96 (br s, 1H), 4.87-4.84 (m, 1H), 4.67-4.44 (m, 9H), 4.33-4.29 (m, 3H), 4.04-4.02 (m, 2H), 3.81-3.79 (m, 2H), 3.49-3.30 (m, 3H), 3.15-3.00 (m, 4H), 2.22 (br s, 1H), 2.18 (br s, 1H), 2.05 (br s, 2H), 1.64-1.61 (m, 3H), 1.49-1.23 (m, 33H), 0.87 (app. t, J=4.0 Hz, 6H); $^{13}$C NMR (100 MHz, CDCl$_3$): δ 166.2 (2C), 166.0, 165.9, 165.8, 165.7, 165.5, 165.2 (2C), 165.0, 164.8, 164.4, 133.4 (2C), 133.2, 133.1, 130.2, 130.1, 130.0, 129.9 (2C), 129.7 (3C), 129.5 (2C), 129.1, 129.0, 128.9 (2C), 128.8, 128.7 (2C), 128.6, 128.5 (3C), 128.3 (2C), 128.2, 128.1, 99.6, 98.7, 97.3, 97.0, 75.3, 75.0, 74.9, 74.3, 73.9, 72.8, 72.5, 71.8, 71.6, 71.3, 71.2, 71.1, 70.6, 70.2, 69.2 (2C), 69.1, 68.2, 67.5, 64.7, 64.1, 62.7, 62.6, 60.5, 46.5, 44.7, 38.6, 37.8, 33.9, 32.1 (2C), 30.1, 29.9, 29.8, 29.7, 29.6, 29.5 (2C), 26.5, 26.4, 22.8, 14.3.

<6-4> Synthesis of D-NBM-C11

According to the general synthetic procedures of deprotection described in Example 1-4, D-NBM-C11 was synthesized with a yield of 90%: $^1$H NMR (400 MHz, CD$_3$OD): δ5.15 (app.t, J=4.4 Hz, 2H), 4.56 (d, J=8.0 Hz, 1H), 4.34 (d, J=8.0 Hz, 1H), 4.25 (br s, 2H), 3.93-3.82 (m, 7H), 3.69-3.53 (m, 13H), 3.43-3.24 (m, 27H), 2.41 (br s, 1H), 2.36 (br s, 1H), 2.22 (br s, 2H), 2.08 (d, J=10.0 Hz, 1H), 1.56 (app. t, J=4.0 Hz, 4H), 1.42-1.22 (m, 37H), 0.90 (t, J=6.4 Hz, 6H); $^{13}$C NMR (100 MHz, CD$_3$OD): δ103.9, 103.6, 103.2, 81.5, 81.4, 78.3, 78.2, 77.8, 77.7, 77.0, 76.8, 75.4, 75.1, 74.9, 74.2, 74.1, 72.4, 72.3, 71.6, 69.5, 69.1, 62.8, 62.3, 48.0, 45.7, 39.9, 35.4, 33.2, 31.0 (2C), 30.9 (2C), 30.8, 30.7, 30.6, 27.6 (2C), 23.9, 14.6; HRMS (EI): calcd. for C$_{55}$H$_{100}$O$_{24}$Na+ [M+Na]+ 1167.6502, found 1167.6500.

EXAMPLE 2

Structure of NBMs

NBMs have a main structure composed of two alkyl chains linked by a norbornene linker as a hydrophobic group and a branched dimaltoside hydrophilic head group. According to spatial orientation of the alkyl chains attached to the linker, the new compound may be classified into two groups, in which one is D-NBM, which is an endo-type (2-endo, 3-endo or 2R, 3S) formed of two alkyl chains linked by a linker, and the other is X-NBM, which is an exo type (2-exo, 3-exo or 2S, 3R).

Since a discrete hydrophobicalkyl group of D-/X-NBM has an internal symmetry plane (compounds A and B of FIG. 3) crossing the center in a long axis direction based on norbornene, D-/X-NBM is an optically-inactive meso compound. Since the alkyl chains are endo or exo type and linked to a central linker, the compounds A and B are diastereomers (i.e., non-mirror image stereoisomers). While final D-/X-NBMs are also diastereomers, they have optical activities due to a lack of a symmetry plane. Since hydrophile-lipophile balance (HLB) is a key variable influencing on properties of an amphiphilic compound, NBMs with various alkyl chain lengths of C9 to C11 were prepared. These novel compounds were synthesized according to four-step synthetic procedures, including dialkylation of norbornene-2,3-dimethanol, dihydroxylation using osmium tetraoxide-N-methyl morpholine-N-oxide (OsO4-NMO), glycosylation using (perbenzoylated maltosyl bromide) and deprotection (FIGS. 1 and 2).

Figure 3:
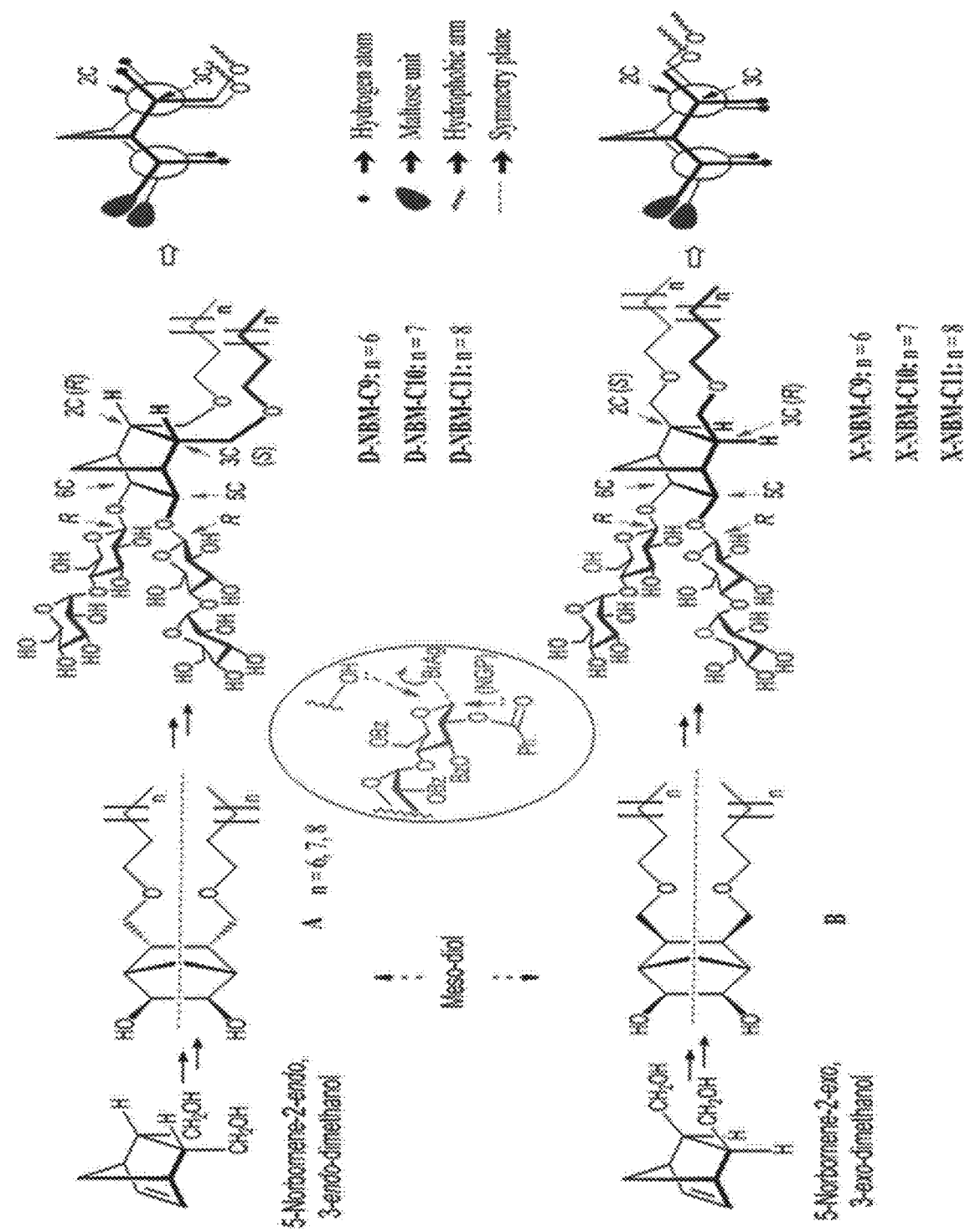
FIG. 3 shows the chemical structures of NBMs and Newman projections thereof, indicating that D-NBMs and X-NBMs are diastereomers for each other.
Figure 4A:
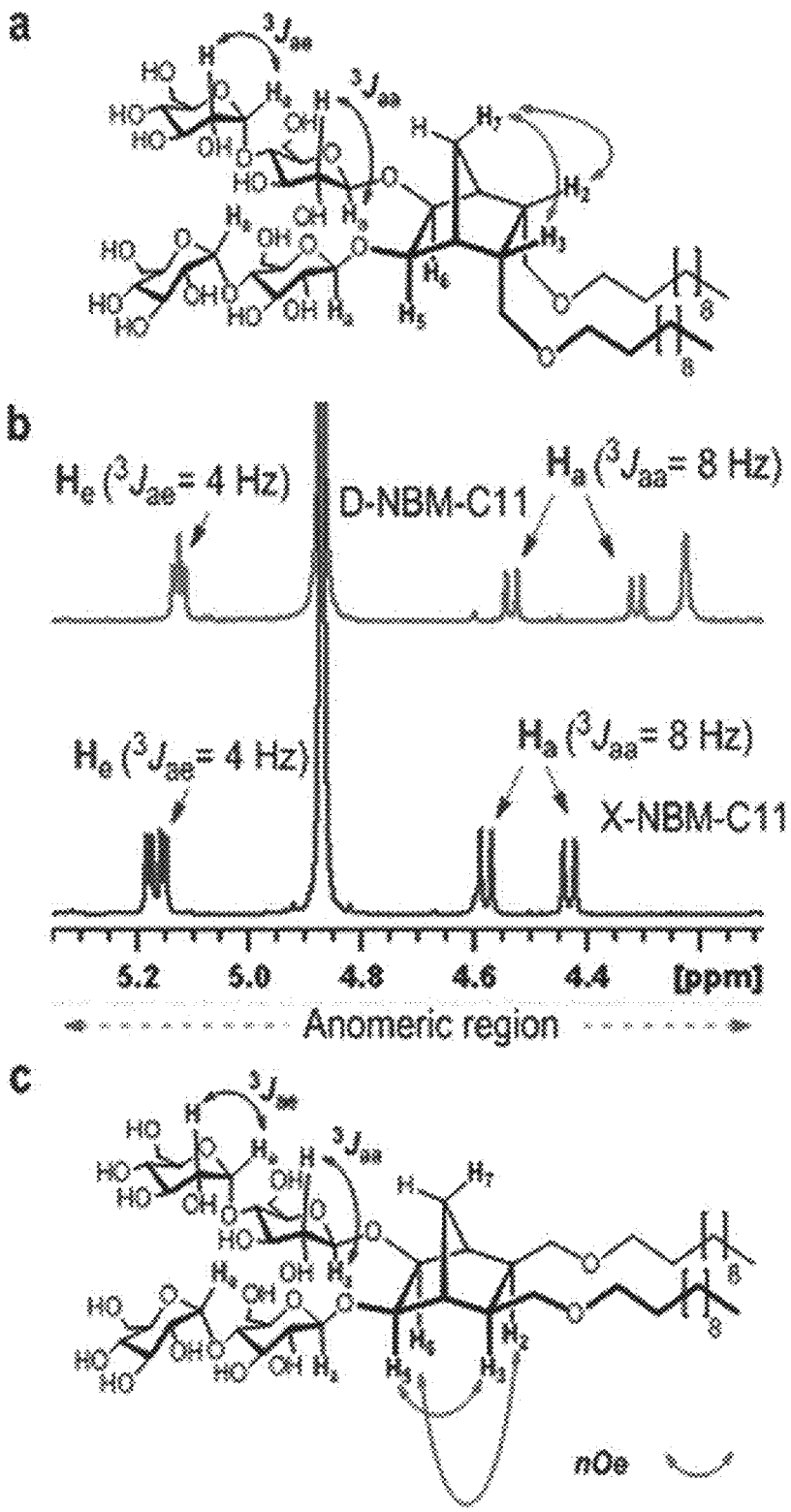
FIG. 4a shows the chemical structures and NMR spectra of D-/X-NBM-C11, illustrating anomeric protons. (a, c) the chemical structure of D-/X-NBM-C11, and (b) partial $^1$H NMR spectra in the anomeric region for D-/X-NBM-C11.
Figure 4B:
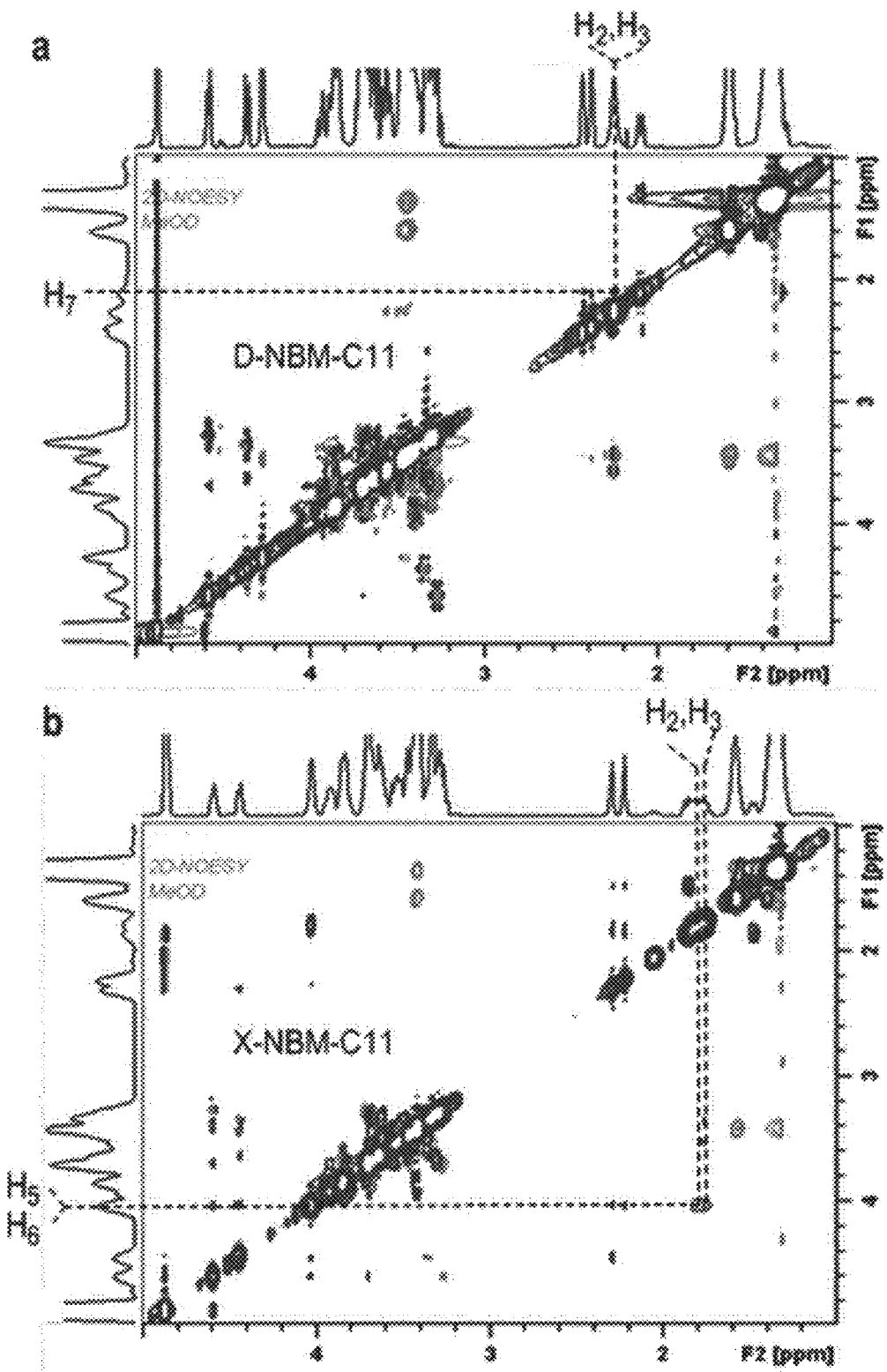
FIG. 4b shows the chemical structures and NMR spectra of D-/X-NBM-C11, illustrating anomeric protons. (a, b) Partial 2D NOESY NMR spectra for D-/X-NBM-C11.

Glycosylation was stereo-specifically performed by taking advantage of neighboring group participation (NGP) of a benzoyl group (FIG. 3). Consequently, the above operation produced individual NBMs having a high diastereomeric purity, which was confirmed from individual $^1$H NMR spectra (FIGS. 4a and 4b). Axial protons of D-NBM-C11 attached to anomeric carbons, named H$_a$, showed two separate $^1$H NMR peaks at 4.55 and 4.33 ppm as doublets (FIG. 4a). Axial protons attached to anomeric carbons of X-NBM-C11 showed two doublet signals in different positions from D-NBM-C11, located at 4.57 and 4.42 ppm. In addition, the vicinal coupling constants ($^3J_{aa}$) for the anomeric protons (H$_a$) of both isomers were 8.0 Hz, which was a typical value of a β-isomer, demonstrating distinct formation of a β-glycosidic bond in the glycosylation. An α-glycosidic bond is differentiated from the β-glycosidic bond in that anomeric protons showed a doublet signal with a smaller coupling constant ($^3J_{ae}$=4.0 Hz) in the region of 5.10 to 5.20 ppm.

This spectrum feature can be identified from another anomeric proton ($H_e$) (FIG. 4a). The exo- or endo-connection of the alkyl chains to the central linker can be confirmed by 2D NOESY spectra of D-/X-NBM-C11 (FIG. 4b). Because of the close proximity in space, the strong NOE correlation signals between proton H7 and protons ($H_2$ and $H_3$) were observed in D-NBM-C11, which were not detected in X-NBM-C11. On the other hand, the strong NOE correlation signals were obtained between protons ($H_2$ and $H_3$) and protons ($H_6$ and $H_5$) for X-NBM-C11, indicating spatial proximity between the protons.

Figure 5:
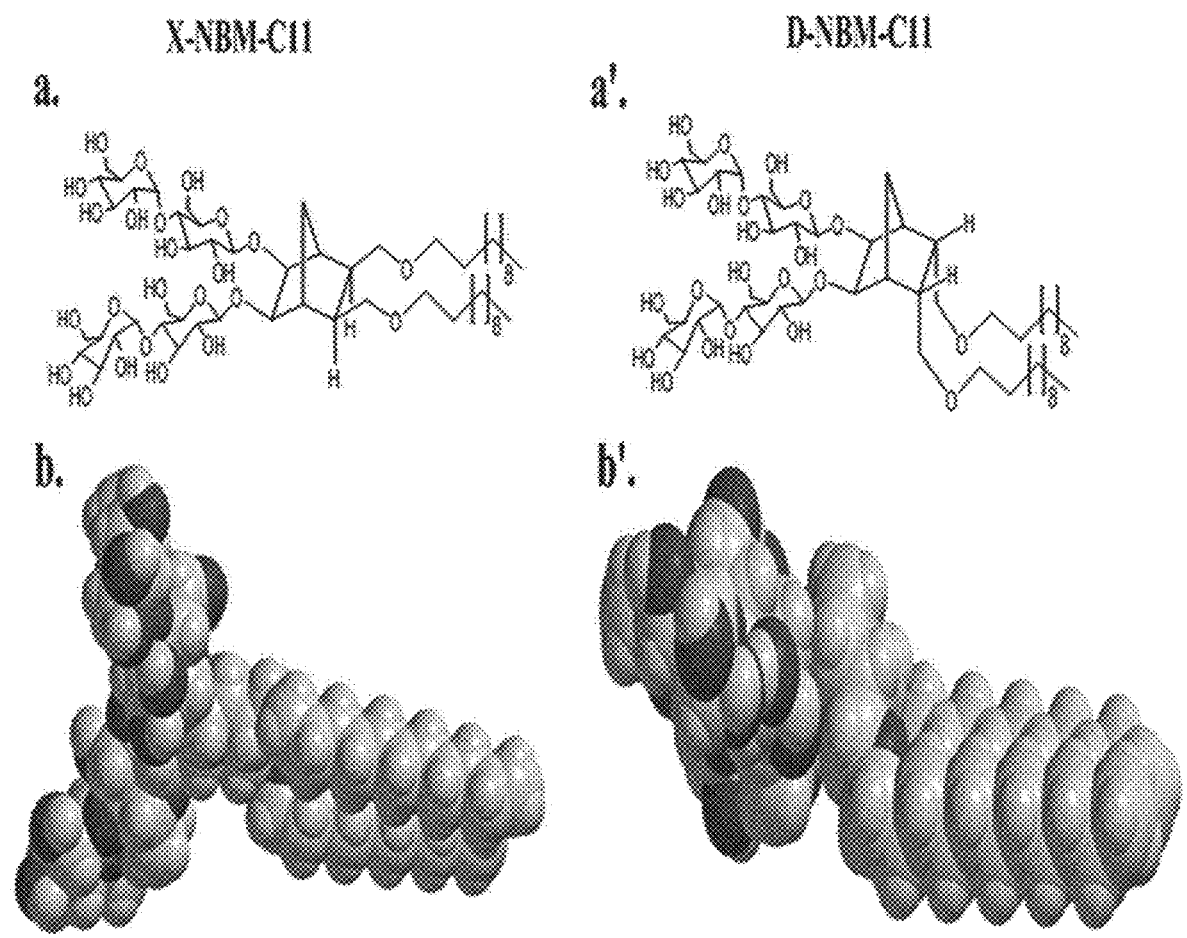
FIG. 5 shows the chemical structures (a and a') and space-filling models (three-dimensional structures; b and b') of D-/X-NBM-C11. The gray large spheres represent carbon atoms, gray small spheres represent hydrogen atoms, and red spheres represent oxygen atoms.

Due to the exo-connection between the alkyl chains and the norbornene linkers, the molecular structure of X-NBM-C11 is more flat and linear than D-NBM-C11, giving a larger interaction between individual amphiphilic compounds in micelles, which seems to also influence on stability of the micelles and stabilization of the membrane proteins (FIG. 5).

EXAMPLE 3

Characteristics of NBMs

To identify the characteristics of NBMs synthesized in Preparation Example 1 to 6 according to the synthetic method of Example 1, molecular weights (MWs) of NBMs, critical micelle concentrations (CMCs) and hydrodynamic radii ($R_h$) of the micelles were measured.

Specifically, the critical micelle concentrations (CMCs) were measured by fluorescent staining with diphenylhexatriene (DPH), and the hydrodynamic radii ($R_h$) of the micelle formed with individual agents (1.0 wt %) were measured by dynamic light scattering (DLS). The measured results compared with a conventional amphiphilic molecule (detergent), DDM, are presented in Table 1.

TABLE 1

| Detergent | M.W. | CMC (mM) | CMC (wt %) | Rh(nm) |
|---|---|---|---|---|
| D-NBM-C9 | 1089.3 | ~0.012 | ~0.0013 | 3.3 ± 0.04 |
| X-NBM-C9 | 1089.3 | ~0.010 | ~0.0011 | 3.7 ± 0.03 |
| D-NBM-C10 | 1117.3 | ~0.008 | ~0.0009 | 3.5 ± 0.03 |
| X-NBM-C10 | 1117.3 | ~0.007 | ~0.0008 | 4.0 ± 0.02 |
| D-NBM-C11 | 1145.4 | ~0.007 | ~0.0008 | 3.7 ± 0.05 |
| X-NBM-C11 | 1145.4 | ~0.006 | ~0.0007 | 17.3 ± 0.10 |
| DDM | 510.1 | ~0.17 | ~0.0087 | 3.4 ± 0.03 |

The CMC values of all NBMs (0.006 to 0.012 mM) were much smaller than that of DDM (0.17 mM). Therefore, since NBMs easily form micelles even at a low concentration, they can exhibit the same or superior effect even with a smaller amount than DDM. In addition, since the CMC values of NBMs were reduced according to an increase in alkyl chain length, which is determined that it is caused by increased hydrophobicity induced by the alkyl chain extension. The sizes of micelles formed with NBMs tended to generally increase as the length of the alkyl chain increases.

In the isomeric comparison, the CMC values of X-NBMs were lower than those of D-NBMs. Such a result indicates that X-NBMs are likely to be more highly self-assembled than D-NBMs. In addition, the sizes of micelles formed by two NBM isomers tended to increase as the length of the alkyl chain increases, because of the change in molecular geometry from conical to cylindrical shape as the alkyl chain length increases. Particularly, this showed that X-NBMs have higher micelle size dependency to the alkyl chain length.

Figure 7A:
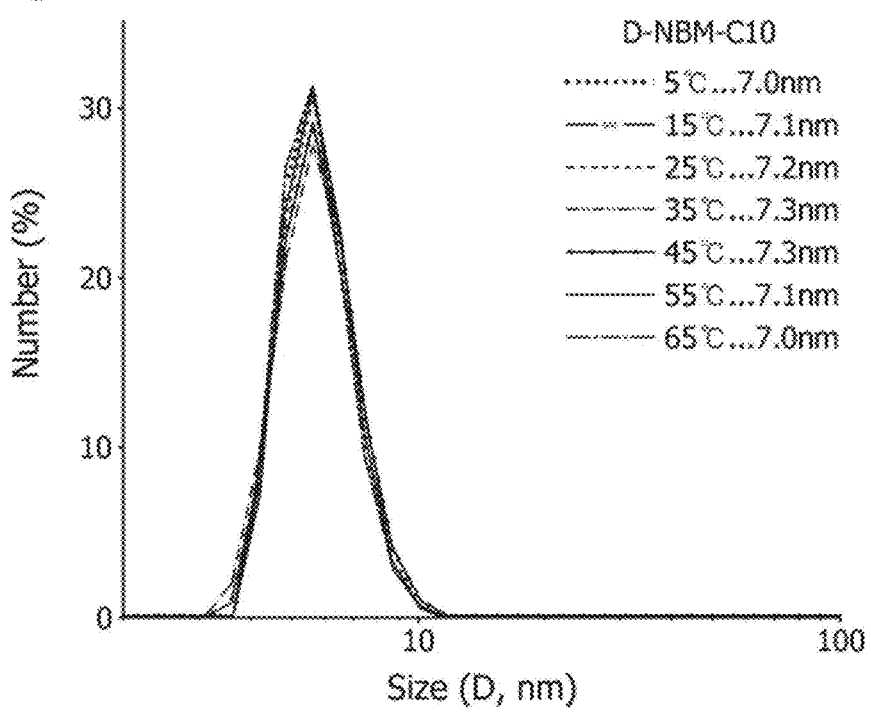
FIG. 7a shows size distribution for micelles according to temperature-dependent changes of D-NBM-C10 (a) and D-NBM-C11 (b)
Figure 7A:
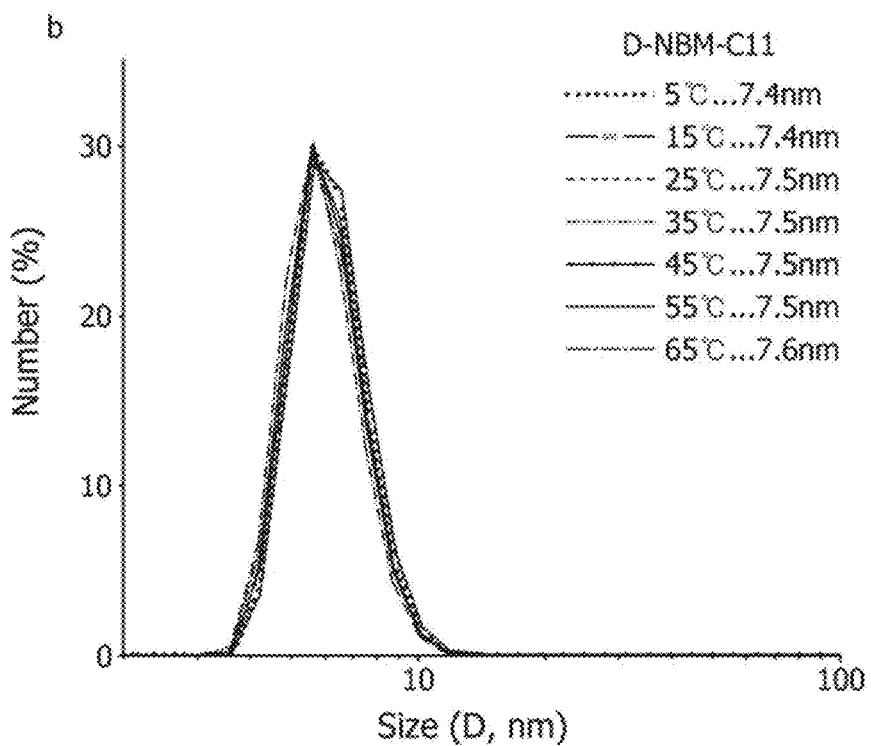
Figure 7B:
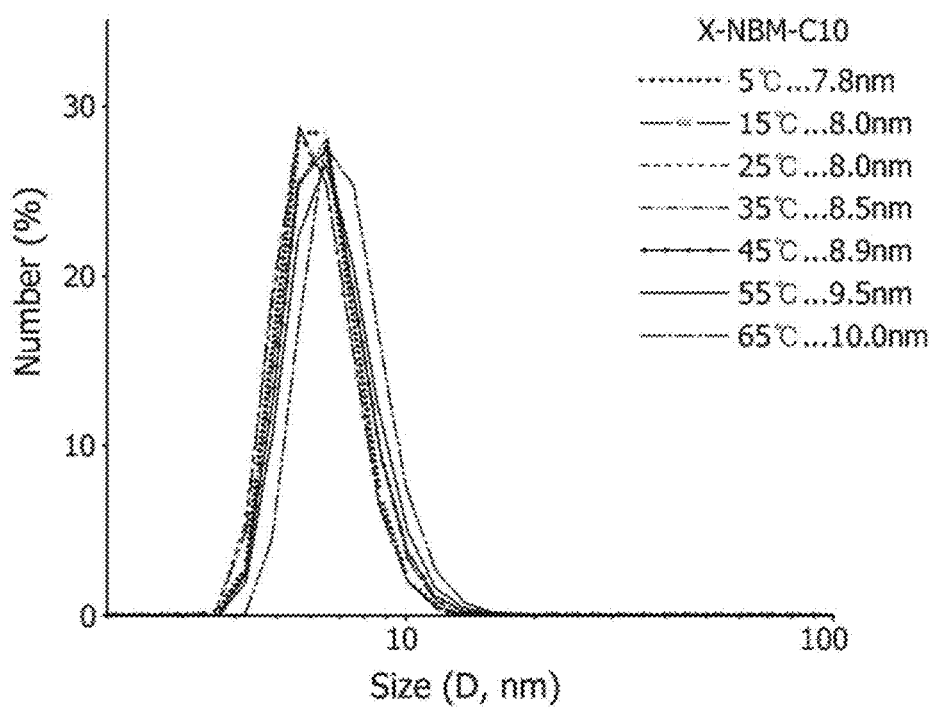
FIG. 7b shows size distribution for micelles according to temperature-dependent changes of X-NBM-C10 (a) and X-NBM-C11 (b)
Figure 7B:
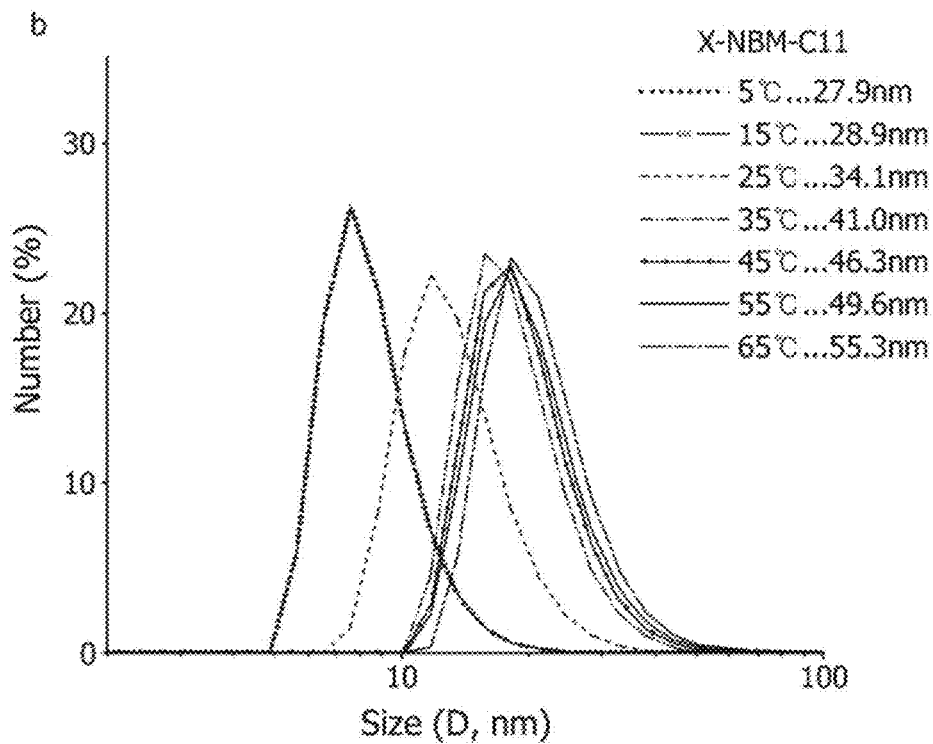

Particularly, as shown in FIGS. 7a and 7b, it was confirmed that the sizes of X-NBM-C11 micelles are changed according to a temperature. Meanwhile, the sizes of D-NBM-C11 micelles were not influenced by a temperature change. It was determined that the above results are deeply related to the membrane protein stability of X-NBM-C11 and D-NBM-C11 induced by the temperature change confirmed in the following examples.

Figure 6A:
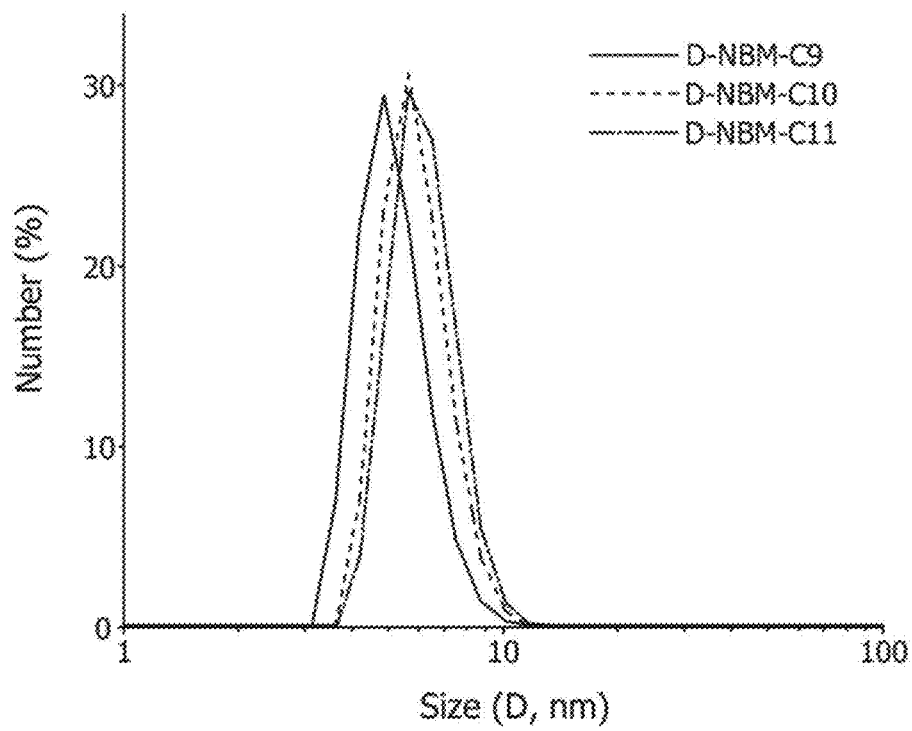
FIGS. 6a and 6b show size distribution at 25° C. for micelles formed by NBMs.
Figure 6B:
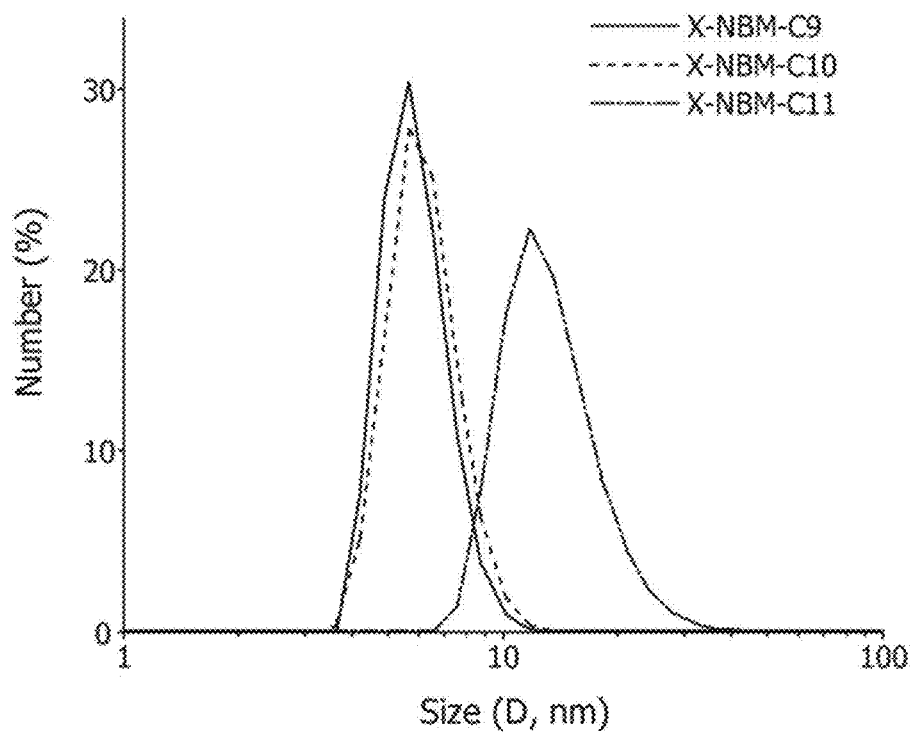

It was considered that the larger micelle size of X-NBMs compared to D-NBMs observed herein results in an increased interaction between amphiphiles by making the structure of a compound as geometrically close to a cylindrical shape, as a result of the linear structure of X-NBMs. This result indicates that a small change in alkyl chain orientation of amphiphilic compounds could generate a large difference in the properties of self-assemblies, which can affect membrane protein research. When the size distribution for micelles of NBM molecules at room temperature (25° C.) was investigated, all isomers showed a single population of micelles, indicating highly uniform micellar structures (FIG. 6).

EXAMPLE 4

Evaluation of UapA Membrane Protein Structural Stabilization Activity of NBMs

An experiment for measuring the structural stability of uric acid-xanthine/H+ symporter (UapA) isolated from *Aspergillus nidulans* using NBMs was performed. The structural stability of UapA was evaluated using sulfhydryl-specific fluorophore, and N-[4-(7-diethylamino-4-methyl-3 to-coumarinyl)phenyl]maleimide (CPM).

Specifically, UapAG411V$_{A1-11}$ (hereinafter, referred to as "UapA") was expressed as GFP fusion in *Saccharomyces cerevisiae* FGY217 strain and isolated in a sample buffer (20 mM Tris (pH 7.5), 150 mM NaCl, 0.03% DDM, 0.6 mM xanthine) according to the method described in the literature written by J. Leung et al. (*Mol. Membr. Biol.* 2013, 30, 32-42). Membranes containing UapA were resuspended in PBS, 10 mM imidazole pH 8.0, 150 mM NaCl, 10% glycerol, and the protein concentration was measured. The membranes were adjusted to a concentration of 1 mg·ml$^{-1}$ and 1 ml aliquots were individually incubated with DDM or NBMs at a final amphiphilic material concentration of 1.0 wt % for 10 minutes at 40° C. 100 μl aliquots were removed from each tube, and a fluorescence reading was taken for each sample before and after ultracentrifugation at 150,000 g for 10 minutes to remove insoluble material. The remaining soluble fraction for each condition was submitted to fluorescent size exclusion chromatography (FSEC) using a Superose 6 column (GE Healthcare) equilibrated with DDM.

Figure 8A:
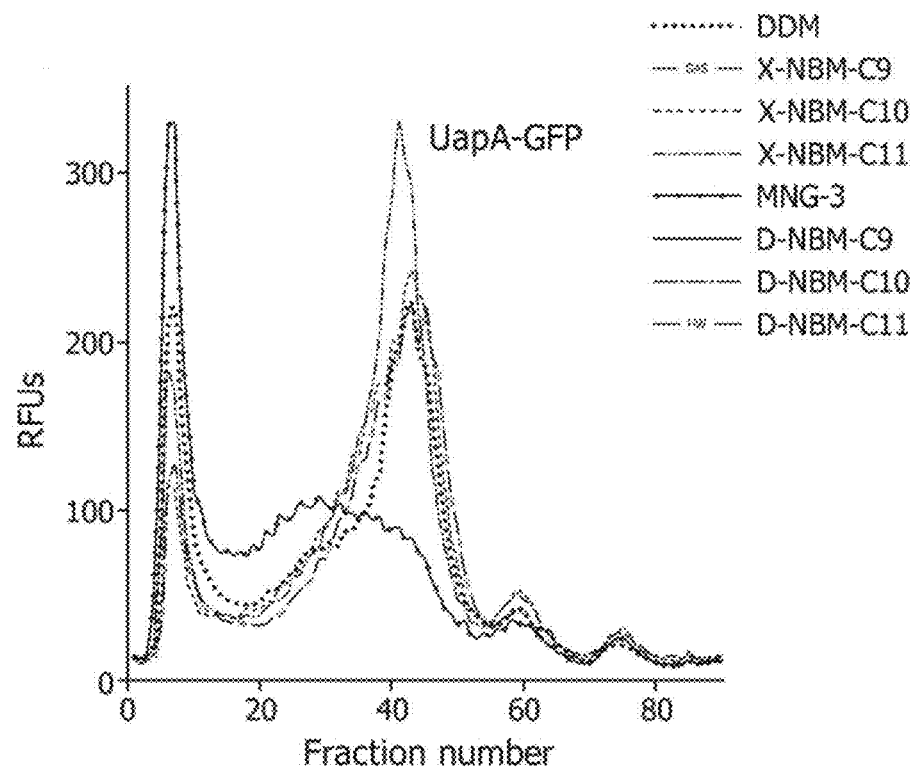
FIGS. 8a and 8b show& thermal stability of UapA proteins solubilized in an aqueous solution with NBMs, MNG-3 or DDM, which is measured by fluorescence size exclusion chromatography (FSEC)
Figure 8B:
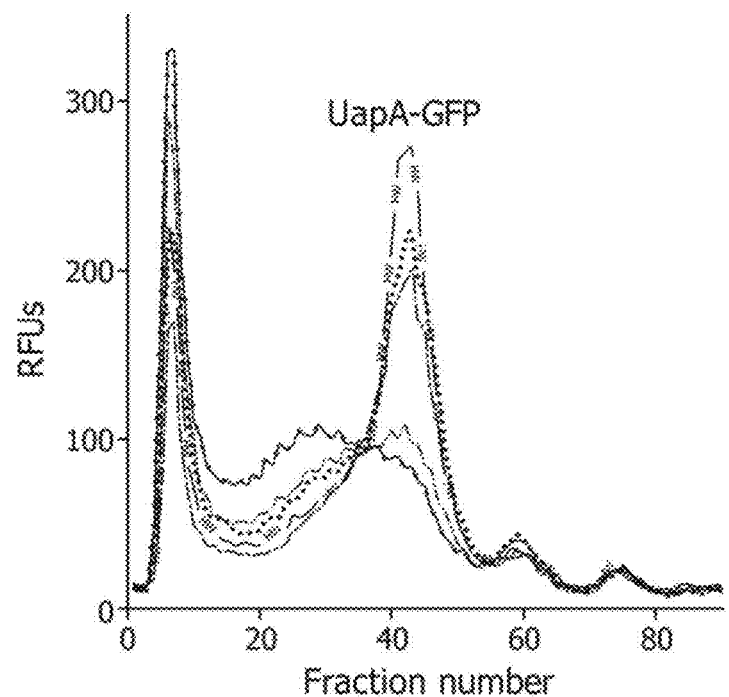

DDM-solubilized UapA-GFP yielded a single monodispersed peak with relatively high intensity (~fraction number 40), implying capability to resist heat denaturation (FIG. 8). When the X-NBMs were evaluated with the transporter, amphiphile efficacy was enhanced with increasing alkyl chain length. X-NBM-C9/C10 was more or less comparable to DDM at retaining the monodispersed protein peak while X-NBM-C11 was substantially better than DDM (FIG. 8a). A similar trend was also observed for D-NBMs. The D-NBMs with the shortest alkyl chain (i.e., D-NBM-C9) showed a low recovery of monodispersed protein peak, indicating that a significant protein aggregation/denaturation had occurred during heating, whereas D-NBM-C10 showed a slightly lower effect than DDM (FIG. 8b). D-NBMs with the longest alkyl chain (i.e., D-NBM-C11) was a little better than DDM. In isomeric comparison, overall performances of X-NBMs were superior to those of D-NBMs. In addition, overall UapA extraction efficiencies of X-NBMs were higher than those of D-NBMs. Particularly, X-NBM-C11 could almost quantitatively extract the transporter from the cell membrane. Interestingly, MNG-3, one of the most successful novel amphiphiles for membrane protein structure research, was ineffective in preventing protein denaturation/aggregation under the same assay conditions (FIGS. 8a and 8b). These results showed that NBMs are used to effectively extract UapA from the cell membranes and exhibit an excellent effect to maintain the extracted protein in a structurally stable state in an aqueous solution, and thus can be effectively used to extract and stabilize membrane proteins.

EXAMPLE 5

Evaluation of Stability of LeuT Membrane Proteins Extracted with NBMs

An experiment for measuring the stability of LeuT protein with NBMs was performed. Concentrations of individual amphiphilic compounds were (a) CMC+0.04 wt % and (b) CMC+0.2 wt %, and the stability of the LeuT protein was evaluated by measuring a LeuT substrate binding activity using [3H]-Leu via scintillation proximity assay (SPA). The measurement was performed at regular intervals during 12-day incubation at room temperature.

Specifically, a wild-type leucine transporter (LeuT) derived from thermophilic bacteria *Aquifex aeolicus* was purified by the method described previously (G. Deckert et al., *Nature* 1998, 392, 353-358). LeuT was expressed in *E. coli* C41 (DE3) transformed with pET16b encoding C-terminally 8× His-tagged transporter (the expression plasmid was provided by Dr E. Gouaux, Vollum Institute, Portland, Oreg., USA). In summary, after isolation of bacterial membranes and solubilization in 1% (w/v) DDM, a protein was bound to $Ni^{2+}$-NTA resin (Life Technologies, Denmark) and eluted in 20 mM Tris-HCl (pH 8.0), 1 mM NaCl, 199 mM KCl, 0.05% (w/v) DDM and 300 mM imidazole. Afterward, the purified LeuT (approximately 1.5 mg/ml) was diluted with ten-fold in identical buffer without DDM and imidazole, but supplemented with NBMs or DDM to reach a final concentration of CMC+0.04% (w/v) or CMC+0.2% (w/v). Protein samples were stored for 12 days at room temperature, and centrifuged at predetermined points of time, the substrate ([3H]-leucine)-binding activity of the transporter was determined via SPA by taking advantage of protein properties. The SPA was performed with a buffer containing 450 mM NaCl and respective NBMs at specified concentrations. The SPA reaction was carried out in the presence of 20 nM [3H]-leucine and 1.25 mg/ml copper chelate (His-Tag) YSi beads (Perkin Elmer, Denmark). Total [3H]-leucine binding for the respective samples was measured using a MicroBeta liquid scintillation counter (Perkin Elmer).

LeuT in all NBMs gave a substantially higher activity of preserving a transporter structure than DDM. The enhanced substrate binding activity of LeuT relative to DDM was well maintained over 12 days for all the NBMs. Therefore, when LeuT was solubilized in X-/D-NBM-C11, the substrate binding activity of the transporter at the end of incubation (t=12 day) was a little less than the initial activity of LeuT solubilized in DDM (FIG. 9a). In addition, it was confirmed that as the concentration of the amphiphile increased, the amphiphilic efficacy of NBMs was further increased, com-pared to DDM (FIG. 9b). Overall, all NBMs were effective in preserving the substrate binding activity of the transporter than DDM.

EXAMPLE 6

Evaluation of Stabilization of the Structures of $\beta_2AR$ Membrane Proteins with NBMs An experiment of measuring the stability of human $\beta_2$ adrenergic receptor ($\beta_2AR$) and G-protein-coupled receptor (GPCR) for NBMs was carried out. That is, the receptor was extracted from the cell membranes by DDM and purified in the same amphiphilic compound. The DDM-purified receptor was diluted in individual DDM- or NBM-containing buffers to adjust the final compound concentration to be CMC+0.2 wt %. The receptor stability was assessed by measuring ligand binding activity using [3H]-DHA.

Consequently, the ligand binding activity of the initial receptor in the NBM-C9s and NBM-C10s was lower than that of DDM, and the ligand binding activity in the presence of NBM-C11s was equivalent to DDM. In addition, X-NBMs showed higher values than all D-NBMs regardless of a chain length (FIG. 10).

<6-1> Long-Term Stability Measurement

To measure long-term stability of human $\beta_2AR$ with NBMs (D-NBM-C11 and X-NBM-C11) showing an excellent ligand binding activity of the receptor in the previous experiment, a radio-labeled ligand binding experiment was performed by the following method. $\beta_2AR$ was purified using 0.1% DDM (D. M. Rosenbaum et al., *Science*, 2007, 318, 1266-1273), and finally concentrated to approximately 10 mg/ml (approximately 200 µM). A main binding mixture containing 10 nM [3H]-DHA supplemented with 0.5 mg/ml BSA was prepared in 0.2% amphiphilic compound (DDM or NBMs (D-NBM-C11 and X-NBM-C11)) using $\beta_2AR$ purified with DDM. The receptor purified with DDM or NBMs was incubated with 10 nM [3H]-DHA at room temperature for 30 minutes. The mixture was loaded onto a G-50 column, the fractions were collected in a 1 ml binding buffer (20 mM HEPES pH 7.5, 100 mM NaCl, containing 0.5 mg/ml BSA and 20× CMC individual amphiphilic compounds). In addition, each fraction was supplemented with a 15 ml scintillation fluid, and receptor-bound [3H]-DHA was measured using a scintillation counter (Beckman) at regular intervals for 3 days. The binding capacity of [3H]-DHA was shown as a bar chart (FIG. 11a).

In addition, $\beta_2AR$ was extracted from the membrane using 1.0 wt % of DDM or X-NBM-C11 and purified at 0.2 wt % for the same individual amphiphilic compounds. Structural stability of the receptor was assessed by ligand binding activity, which was measured with sample aliquots at regular intervals during 7-day incubation at room temperature. Each experiment was carried out in triplicate (FIG. 12b).

As a result, it was confirmed that the receptor solubilized in DDM has excellent initial ligand binding activity, but the binding activity rapidly decreased over time. However, D-NBM-C11 or X-NBM-C11 well retained the long-term ligand binding activity of the receptor (FIG. 11a). Particularly, the receptor solubilized in X-NBM-C11 had the highest ligand binding retention property (FIGS. 11a and 12b). The same result was obtained as the above result when the receptor was directly extracted from the cell membrane using DDM or X-NBM-C11 (FIG. 12).

<6-2> Size Exclusion Chromatography (SEC)

$\beta_2$AR purified with 0.1 wt % DDM was loaded onto an M1 Flag column in the presence of 2 mM $\beta_2$AR, and the column was washed with a DDM or X-NBM-C11 buffer (20 mM HEPES pH 7.5, 100 mM NaCl, 0.2% respective amphiphile). The receptor was eluted in 20× CMC DDM or X-NBM-C11 containing 5 mM EDTA and 0.2 mg/ml free Flag peptide. The eluate was further applied to a superdex-200 10/300 GL column (GE healthcare) at 0.5 ml/min, and UV absorbance at 280 nm was recorded. The running buffer contained 20 mM HEPES pH 7.5, 100 mM NaCl, 20× CMC individual detergents (DDM and X-NBM-C11).

In addition, GPCR-$G_s$ complex purified in DDM was replaced with X-NBM-C11 through amphiphilic molecule exchange, and sample aliquots were obtained at regular intervals in 21-day incubation at 4° C. to measure complex stability.

Consequently, as shown in FIG. 13, X-NBM-C11 formed homogeneous PDCs with the same size as that formed by DDM. In addition, SEC profiles for 21 days revealed that X-NBM-C11 perfectly maintained complex stability under these conditions (FIG. 11b).

<6-3> $G_s$-Protein Coupling Assay

To investigate a protein function, the receptor was conjugated with a fluorophore (monobromobimane; mBBr). The mBBr-$\beta_2$AR was used to monitor the conformational changes of the receptor in the presence of binding partners (isopreoterenol (ISO) and $G_s$-protein) through fluorescence measurement, and detailed experimental methods are as follows.

0.5 μl undispersed mBBr-labeled receptor at 50 μM in DDM was diluted with 500 μl 0.1% NBM or DDM-containing buffer, and incubated for 15 minutes at room temperature, thereby obtaining a receptor having a final concentration of 50 nM. 2 μM isoproterenol (ISO) was added and the resulting solution was further incubated for 15 minutes at room temperature. After addition of 250 nM $G_s$, the protein samples were further incubated at room temperature for 20 minutes. Bimane fluorescence was measured by excitation at 370 nm, and emission spectra were recorded from 430 nm to 510 nm in a unit of 1 nm increments with 0.5 nm/s integration on a Spex FluoroMax-3 spectrofluorometer (Jobin Yvon Inc.) in photon counting mode set at 4-nm emission bandwidth pass. The mBBr response in 0.1% DDM was used as a positive control. The data show a representative in three independent experiments (FIG. 14).

Consequently, in the absence of ISO, DDM- or X-NBM-C11-solubilized receptor showed fluorescence emission spectra corresponding to an inactive receptor. When ISO was added, the fluorescence emission spectra noticeably changed in emission intensity and maximum wavelength (kmax) reflecting partial receptor activation in both amphiphilic compounds. When $G_s$ protein and ISO were simultaneously added to the receptor, a further spectral change corresponding to full receptor activation was observed (FIG. 14).

These results indicate that the receptor solubilized in X-NBM-C11 undergoes conformational changes into the partially active (with ISO alone) or fully active states (with ISO+$G_s$) as occurring in DDM. Therefore, it was confirmed that the receptor solubilized in X-NBM-C11 also retains an original protein function.

<6-4> Negative Stain EM Analysis of $\beta_2$AR-$G_s$ Complex Solubilized in X-NBM-C11

A $\beta_2$AR-$G_s$ protein complex was prepared for electron microscopy using the conventional negative staining protocol, and imaged at room temperature with a Tecnai T12 electron microscope operated at 120 kV using low-dose procedures. Images were recorded at a magnification of 71,138× and a defocus value of approximately 1.4μ using a Gatan US4000 CCD camera. All images were binned (2×2 pixels) to obtain a pixel size of 4.16 A at the specimen level. Particles were manually excised using e2boxer (part of the EMAN2 software suite). 2D reference-free alignment and classification of particle projections were performed using ISAC. 14,556 projections of $\beta_2$AR-$G_s$ were subjected to ISAC, producing 199 classes consistent over two-way matching and accounting for 10,100 particle projections.

Consequently, while the $\beta_2$AR-$G_s$ protein complex isolated in DDM had aggregated particles, the $\beta_2$AR-$G_s$ complex isolated in X-NBM-C11 produced highly mono-dispersed particles (FIG. 15a). In addition, individual components of the complex ($\beta_2$AR, $G_{\alpha s}$ and $G_{\beta \gamma}$) were clearly distinguished in representative 2D class images (FIGS. 15b and 15c). $G_\alpha$ (Ras and α-helical (AH) domains) and individual $G_\beta$ and G subunits were discernable in X-NBM-C11. It indicates that the amphiphilic compound of the present invention has a significant potential for the explanation of dynamic conformational changes of membrane protein complexes through EM analysis.

EXAMPLE 7

Evaluation of NBM Activity for Structural Stabilization of MelB$_{st}$ Membrane Proteins An experiment of measuring structural stability of MelB$_{st}$ (*Salmonella typhimurium* melibiose permease) protein with NBMs was carried out. The MelB$_{St}$ protein was extracted from the membrane using NBMs or DDM, and the amounts and structure of the extracted proteins were analyzed by SDS-PAGE and western blotting. The concentration of the used amphiphilic compound was 1.5 wt %. The proteins were extracted at four temperatures (0, 45, 55, and 65° C.) and incubated at the same temperature for 90 minutes, and the amounts of the remaining proteins solubilized in an aqueous solution were measured, so as to simultaneously evaluate both performances of the compound such as protein extraction efficiency and stabilization activity. The amounts of the proteins extracted and stabilized by respective amphiphilic molecules were represented as relative values (%) to the amounts of total proteins contained in the membrane sample not treated with an amphiphilic molecule.

Specifically, *Salmonella typhimurium* melibiose permease (MelB$_{St}$) with a C-terminal 10-His tag was expressed in *E. coli* DW2 cells ($^\Delta$melB and $^\Delta$lacZY) using plasmid pK95$^\Delta$AHB/WT MelB$_{St}$/CH10. Cell growth and membrane preparation were carried out according to the method described in the literature written by A. S. Ethayathulla et al. (*Nat. Commun.* 2014, 5, 3009). Protein assays were carried out with a Micro BCA kit (Thermo Scientific, Rockford, Ill.). The measurement of MelB$_{St}$ stability was carried out on NBMs or DDM according to the protocol described by P. S. Chae et al. (*Nat. Methods* 2010, 7, 1003-1008). Membrane samples containing MelB$_{St}$ (final protein concentration was 10 mg/mL) were incubated with a solubilization buffer (20 mM sodium phosphate, pH 7.5, 200 mM NaCl, 10% glycerol, 20 mM melibiose) and 1.5% (w/v) of DDM or NBMs (X-NBM-C10, D-NBM-C10, X-NBM-C11 or D-NBM-C11) at four different temperatures (0, 45, 55, 65° C.) for 90 minutes. To remove insoluble materials, following ultracentrifugation at 355,590 g using a Beckman Optimal™ MAX ultracentrifuge with TLA-100 rotor for 45 minutes at 4° C. was performed, and 20 μg of each protein sample was separated by SDS-16% PAGE, and then immunoblotted with a Penta-His-HRP antibody (Qiagen, Germantown, Md.). MelB$_{St}$ was detected using SuperSignal West Pico chemiluminescent substrate by an ImageQuant LAS 4000 Biomolecular Imager (GE Health Care Life Science).

As shown in FIG. 16, DDM showed high MelB$_{St}$ protein extraction efficiency at 0° C. and 45° C. NBMs had a slightly lower efficiency of solubilizing proteins from the membrane at 0° C. and 45° C. than DDM.

However, when the temperature was raised to 55° C., D-NBMs of NBMs produced a larger amount of solubilized proteins than DDM, effectively extracted the MelB$_{St}$ protein, and maintained the solubility of the extracted MelB$_{St}$ to be excellent. At 65° C., no MelB$_{St}$ protein solubilized in an aqueous solution was detectable in either DDM or NBMs.

Overall, at a low temperature (0° C.), DDM showed a higher protein extraction efficiency than NBMs, but at a relatively high temperature (45° C.), NBMs showed a similar efficiency than DDM, and at a higher temperature (55° C.), NBMs showed a higher efficiency. This result indicated that DDM was excellent in terms of the protein extraction efficiency, but NBMs were superior in terms of protein stabilization activity. In addition, among isomers of NBMs, D-NBMs, particularly, D-NBM-C10 and D-NBM-C11 showed an excellent membrane protein stabilization activity.

By using a norbornene-based compound according to embodiments of the present invention, compared to a conventional compound, membrane proteins can be stably stored in an aqueous solution for a long time, and thus can be used in structural and functional analyses thereof.

The structural and functional analyses of the membrane proteins are one of the most noticeable field in biology and chemistry, and can be applied in research on a protein structure closely related to development of a novel drug.

In addition, the compound according to the embodiments of the present invention has a small size when forming a complex with membrane proteins, and thus can obtain high-quality membrane protein crystals, thereby stimulating crystallization.

In addition, the compound according to the embodiments of the present invention can be synthesized from start materials that can be easily obtained by a simple method, and mass-produced for membrane protein research.

Above, the present invention has been described with reference to exemplary examples, but it can be understood by those of ordinary skill in the art that the present invention may be changed and modified in various forms without departing from the spirit and scope of the present invention which are described in the accompanying claims.

What is claimed is:

1. A compound represented by Formula 1 or 2:

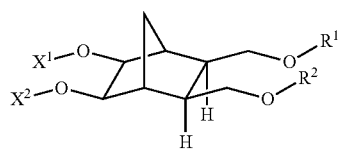

[Formula 1]

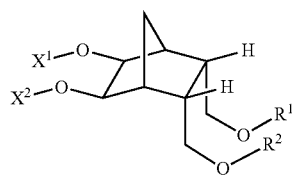

[Formula 2]

Wherein each of $R^1$ and $R^2$ is independently a substituted or unsubstituted $C_3$ to $C_{30}$ alkyl group, a substituted or unsubstituted $C_3$ to $C_{30}$ cycloalkyl group, or a substituted or unsubstituted $C_3$ to $C_{30}$ aryl group; and $X^1$ and $X^2$ are saccharides.

2. The compound of claim 1, wherein the saccharide is a monosaccharide or a disaccharide.

3. The compound of claim 1, wherein the saccharide is glucose or maltose.

4. The compound of claim 1, wherein each of the $R^1$ and $R^2$ is independently a substituted or unsubstituted $C_3$ to $C_{30}$ alkyl group; and the $X^1$ and $X_2$ are maltose.

5. The compound of claim 1, wherein the compound is one of Formulas 3 to 7 as follows:

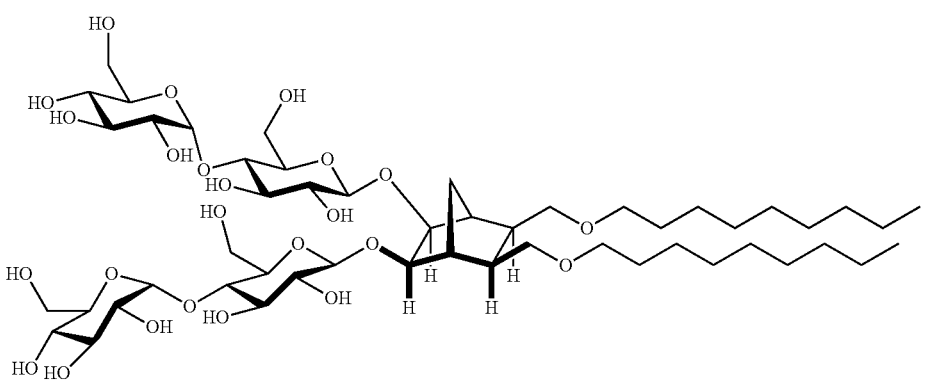

[Formula 3]

-continued
[Formula 4]
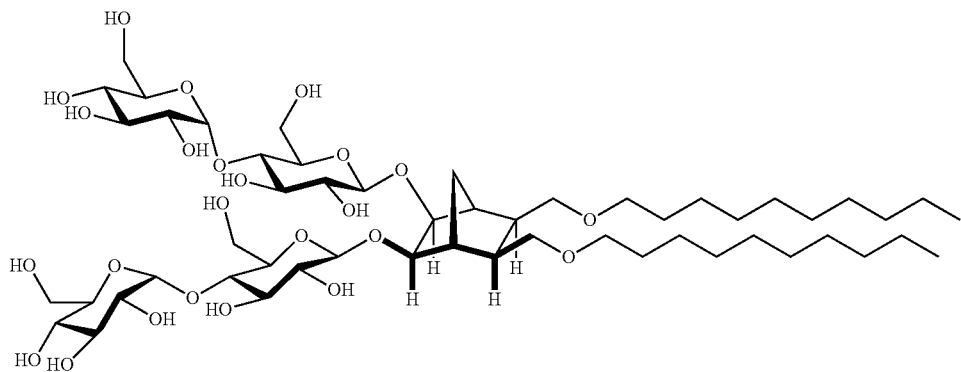
[Formula 5]
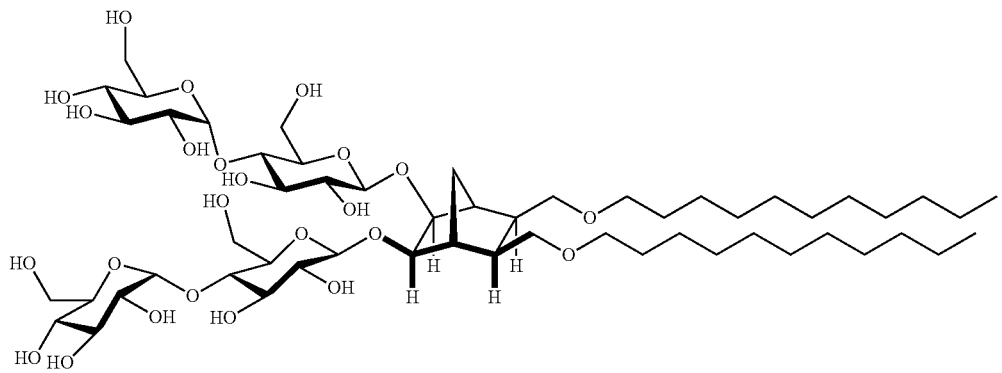
[Formula 6]
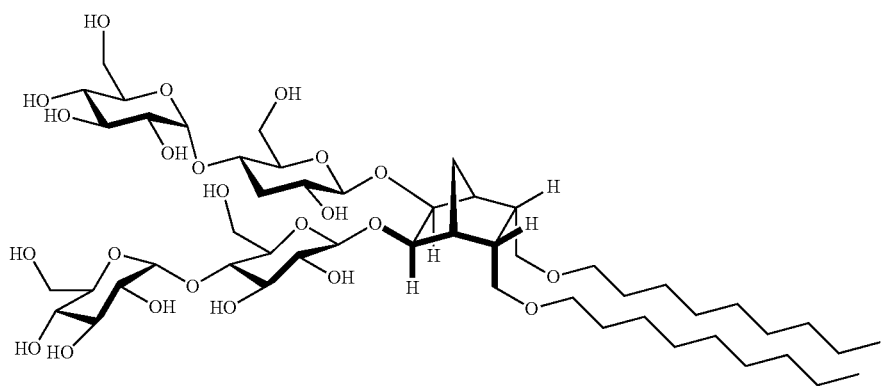
[Formula 7]
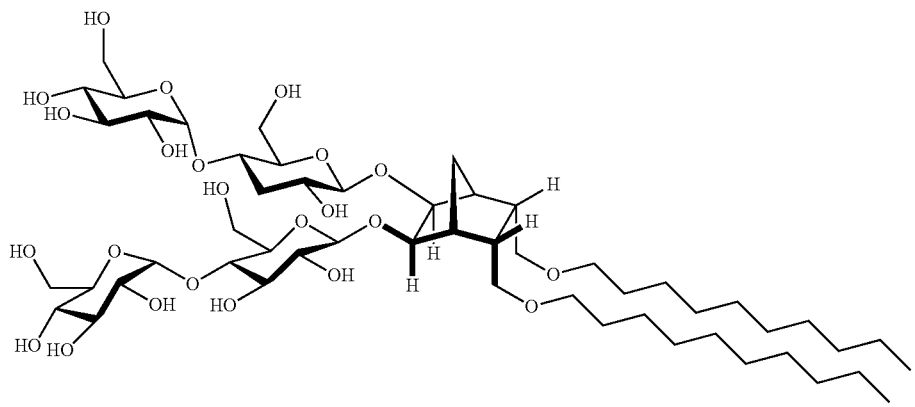

[Formula 8]

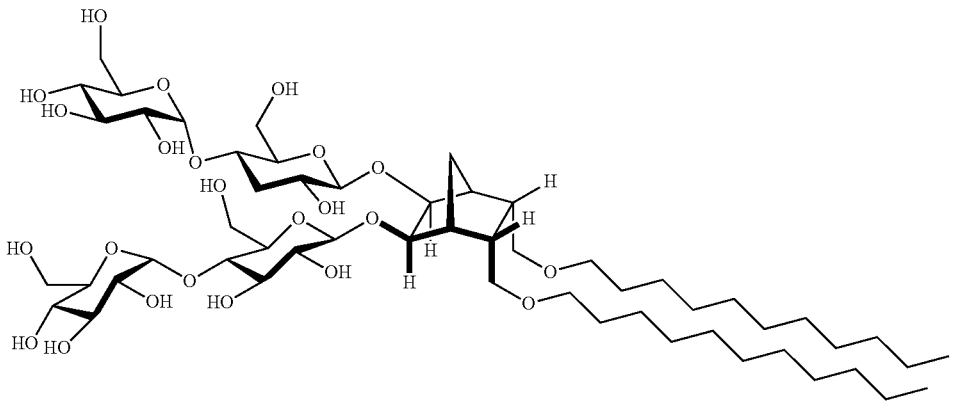

6. The compound of claim 1, wherein the compound is an amphiphilic molecule for extracting, solubilizing, stabilizing, crystallizing or analyzing a membrane protein.

7. The compound of claim 1, wherein the compound has a critical micelle concentration (CMC) in an aqueous solution of 0.0001 to 1 mM.

8. A composition for solubilizing, stabilizing, crystallizing or analyzing a membrane protein, comprising the compound of claim 1.

9. The composition of claim 8, wherein the composition is prepared in the form of micelles, liposomes, emulsion or nanoparticles.

10. A method for preparing a compound represented by Formula 1 or 2, comprising:
1) introducing an alkyl group through dialkylation of 5-norbornene-2-exo, 3-exo-dimethanol or 5-norbornene-2-endo, 3-endo-dimethanol as a diastereomer thereof
2) converting a double bond in norbornene into a diol through dihydroxylation of the product obtained in operation 1);
3) introducing a saccharide with protective group through glycosylation of the product obtained in operation 2); and
4) performing deprotection of the product obtained in operation 3):

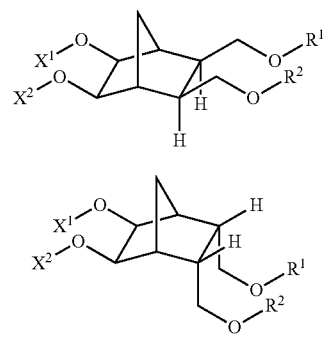

[Formula 1]

[Formula 2]

where each of $R^1$ and $R^2$ is independently a substituted or unsubstituted $C_3$ to $C_{30}$ alkyl group, a substituted or unsubstituted $C_3$ to $C_{30}$ cycloalkyl group, or a substituted or unsubstituted $C_3$ to $C_{30}$ aryl group; and
$X^1$ and $X^2$ are saccharides.

11. The method of claim 10, wherein each of the $R^1$ and $R^2$ is independently a substituted or unsubstituted $C_3$ to $C_{30}$ alkyl group; and $X^1$ and $X^2$ are maltose.

12. The method for solubilizing, stabilizing, crystallizing or analyzing a membrane protein, comprising:
treating a membrane protein with a compound of Formula 1 or 2 in an aqueous solution:

[Formula 1]

[Formula 2]

where each of $R^1$ and $R^2$ is independently a substituted or unsubstituted $C_3$ to $C_{30}$ alkyl group, a substituted or unsubstituted $C_3$ to $C_{30}$ cycloalkyl group, or a substituted or unsubstituted $C_3$ to $C_{30}$ aryl group; and
$X^1$ and $X^2$ are saccharides.

13. The method of claim 12, wherein each of the $R^1$ and $R^2$ is independently a substituted or unsubstituted $C_3$ to $C_{30}$ alkyl group; and the $X^1$ and $X^2$ are glucoses or maltose.

14. The method of claim 12, wherein the membrane protein is uric acid-xanthine/$H^+$ symporter (UapA), leucine transporter (LeuT), human $\beta_2$ adrenergic receptor ($\beta_2$AR), melibiose permease (MelB$_{st}$), or a combination of two or more thereof.

* * * * *

UNITED STATES PATENT AND TRADEMARK OFFICE
CERTIFICATE OF CORRECTION

PATENT NO. : 11,279,726 B2
APPLICATION NO. : 16/480348
DATED : March 22, 2022
INVENTOR(S) : Pil Seok Chae et al.

It is certified that error appears in the above-identified patent and that said Letters Patent is hereby corrected as shown below:

On the Title Page

Item (73) Assignee, first line:
"Industry-Usiversity Cooperation Foundation Hanyang University Erica Campus"
Should be changed to:
--Industry-University Cooperation Foundation Hanyang University Erica Campus--

Signed and Sealed this
Twelfth Day of July, 2022

Katherine Kelly Vidal
*Director of the United States Patent and Trademark Office*